US005997869A

United States Patent [19]
Goletz et al.

[11] Patent Number: 5,997,869
[45] Date of Patent: Dec. 7, 1999

[54] PEPTIDES CONTAINING A FUSION JOINT OF A CHIMERIC PROTEIN ENCODED BY DNA SPANNING A TUMOR-ASSOCIATED CHROMOSOMAL TRANSLOCATION AND THEIR USE AS IMMUNOGENS

[75] Inventors: Theresa J. Goletz, Kensington; Jay A. Berzofsky; Lee J. Helman, both of Bethesda, all of Md.

[73] Assignee: The United States of America as represented by the Department of Health and Human Services, Washington, D.C.

[21] Appl. No.: 08/528,129

[22] Filed: Sep. 14, 1995

Related U.S. Application Data

[63] Continuation-in-part of application No. 08/424,573, Apr. 17, 1995, which is a continuation of application No. 08/031,494, Mar. 15, 1993, abandoned.

[51] Int. Cl.$^6$ .......................... A61K 39/00; A61K 38/00; A61K 38/04
[52] U.S. Cl. .................................... 424/184.1; 424/185.1; 424/192.1; 530/300; 530/326; 530/327
[58] Field of Search .................................. 530/300, 326; 424/184, 185.1, 277.1; 514/2

[56] References Cited

PUBLICATIONS

Abastado et al., "Fine Mapping of Epitopes by Intradomain $K^d/D^d$ Recombinants," *Journal of Experimental Medicine*, 166:327–340 (Aug. 1987).
Aichele et al., "Antiviral Cytotoxic T Cell Repsonse Induced by in Vivo Priming With a Free Synthetic Peptide," *J. Exp. Med.*, 171:1815–1820 (May 1990).
Alexander et al., "Correlation Between CD8 Dependency and Determinant Density Using Peptide–Induced, $L^d$–restricted Cytotoxic T Lympphocytes," *J. Exp. Med.*, 173:849–858 (Apr. 1991).
Ashwell et al., "Antigen Presentation by Resting B Cells Radiosensitivity of the Antigen–Presentation Function and Two Distinct Pathways of T Cell Activation," *J. Exp. Med.*, 159:881–905 (Mar. 1984).
Bennink et al., "Recombinant Vaccinia Virus Primes and Stimulates Influenza Haemagglutinin–Specific Cyto–Toxic T Cells," *Nature*, 311:578–579 (Oct. 1994).
Bhattacharya et al., "A Shared Alloantigenic Determinant on Ia Antigens Encoded by the I–A and I–E Sub–Regions: Evidence . . . ," *The Journal of Immunology*, 127:2488–2495 (Dec. 1981).
Boog et al., "Role of Dendritic Cells in the Regulation of Class I Restricted Cytotoxic T Lymphocyte Responses," *The Journal of Immunology*, 140:3331–3337 (May 15, 1988).
Carbone et al., "Induction of Cytotoxic T Lymphocytes by Primary in Vitro Stimulation With Peptides," *J. Exp. Med.*, 167:1767–1779 (Jun. 1988).
Caron et al., "TP53 Tumor Suppressor Gene: A Model for Investigating Human Mutagenesis," *Genes, Chromosomes & Cancer*, 4:1–15 (1992).
Cease et al., "T Cell Clones Specific for an Amphipathic α–Helical Region of Sperm Whale Myoglobin Show Differing Fine Specificies for Synthetic Peptides," *J. Exp. Med.*, 164:1779–1784 (Nov. 1986).
Ceredig et al., "Expression of Interleukin–2 Receptors as A Differentiation Marker on Intrathymic Stem Cells," *Nature*, 314:98–100 (Mar. 1985).
Chakrabarti et al., "Expression of the HTLV–III Envelope Gene by a Recombinant Vaccinia Virus," *Nature*, 320:535–537 (Apr. 1986).
Chen et al., "Human Papillomavirus Type 16 Nucleoprotein E7 is a Tumor Rejection Antingen," *Proc. Natl. Acad. Sci. USA* 88:110–114 (Jan. 1991).
Chesnut et al., "Studies on the Capacity of B Cells to Serve as Antigen–Presenting Cells," *The Journal of Immunology*, 126:1075–1079 (Mar. 1981).
Chiba et al., "Mutations in the p53 Gene are Frequent in Primary, Resected Non–Small Cell Lung Cancer," *Oncogene*, 5:1603–1610 (1990).
Chung et al., "Probing the Structure and Mechanism of Ras Protein with an Expanded Genetic Code," *Science*, 259:806–809 (Feb. 5, 1993).
Clerici et al., "Detection of Cytotoxic T Lymphocytes Specific for Synthetic Peptides of gp160 in HIV–Seropositive Individuals," *The Journal of Immunology*, 146:2214–2219 (Apr. 1, 1991).
Cornette et al., "Identification of T–Cell Epitopes and Use in Construction of Sythetic Vaccines," *Methods in Enzymology*, 178:611–634 (1989).
D'Amico et al., "High Frequency of Somatically Acquired p53 Mutations in Small–Cell Lung Cancer Cell Lines and Tumors," *Oncogene*, 7:339–346 (Feb. 1992).
Debrick et al., "Macrophages as Accessory Cells for Class I MHC–Restricted Immune Responses," *The Journal of Immunology*, 147:2846–2851 (Nov. 1, 1991).
DeLisi et al., "T–Cell Antigenic Sites Tend to be Amphipathic Structures," *Proc. Natl. Acad. Sci. USA*, 82:7048–7052 (Oct. 1985).
Deres et al., "In Vivo Priming of Virus–Specific Cytotoxic T Lymphocytes with Synthetic Lipopeptide Vaccine," *Nature*, 342:561–564 (Nov. 30, 1989).
Deres et al., "Preferred Size of Peptides That Bind to H–2 $K^b$ is Sequence Dependent," *Eur. J. Immunol.*, 22:1603–1608 (Jun. 1992).

(List continued on next page.)

*Primary Examiner*—Laurie Scheiner
*Assistant Examiner*—Jeffrey S. Parkin
*Attorney, Agent, or Firm*—Fish & Richardson P.C.

[57] ABSTRACT

A method of immunizing a mammal against a tumor cell by exposing splenic or peripheral blood mononuclear cells to a peptide that encompasses a fusion joint of a fusion protein encoded by DNA spanning a human chromosomal translocation associated with Ewing's sarcoma (t(11;22)(q24;q12)) or alveolar rhabdomyosarcoma (t(2:13)(q35;q14)) is provided.

22 Claims, 15 Drawing Sheets

OTHER PUBLICATIONS

Evans et al., "Structure and Expression of a Mouse Major Histocompatibility Antigen Gene, H–2L$^d$," *Proc. Natl. Acad. Sci. USA* 79:1994–1998 (Mar. 1982).

Falk et al., "Allele–Specific Motifs Revealed by Sequencing of Self–Peptides Eluted from MHC Molecules," *Nature*, 351:290–296 (May 23, 1991).

Fremont et al., "Crystal Structures of Two Viral Peptides in Complex with Murine MHC Class I H–2k$^b$," *Science*, 257:919–926 (Aug. 14, 1992).

Gao et al., "Priming of Influenza Virus–Specific Cytotoxic T Lymphocytes Vivo by Short Synthetic Peptides," *Journal of Immunolgoy*, 147:3268–3273 (Nov. 15, 1991).

Germain, "The Ins and Outs of Antigen Processing and Presentation," *Nature*, 322:687–689 (Aug. 1986).

Goudsmit et al., "Human Immunodeficiency Virus Type 1 Neutralization Epitope With Conserved Architecture Elicits Early Type–Specific Antibodies in . . . ," *Proc. Natl. Acad. Sci. USA*, 85:4478–4482 (Jun. 1988).

Guo et al., "Different Length Peptides Bind to HLA–Aw68 Similarly at Their Ends but Bulge Out in the Middle," *Nature*, 360:364–366 (Nov. 26, 1992).

Hart et al., "Priming of Anti–Human Immunodeficiency Virus (HIV) CD8+ Cytotoxic T Cells In Vivo by Carrier––Free HIV Synthetic Peptides," *Proc. Nat. Acad. Sci. USA*, 88:9448–9452 (Nov. 1991).

Harty et al., "CD8+ T Cells Specfiic for a Single Nonamer Epitope of Listeria Monocytogenes Are Protective In Vivo," *J. Exp. Med.*, 175:1531–1538 (Jun. 1992).

Inaba et al., "Dendritic Cells Pulsed with Protein Antigens In Vitro Can Prime Antigen–Specific, MHC–Restricted T Cells In Situ," *J. Exp. Med.*, 172:631–640 (Aug. 1990).

Jung et al., "Human T–Lymphocytes Recognize a Peptide of Single Point–Mutated, Oncogenic ras Proteins," *J. Exp. Med.*, 173:273–276 (Jan. 1991).

Kast et al.,"Failure or Success in the Restoration of Virus–Specific Cytotoxic T Lymphocyte Response Defects by Dendritic Cells," *The Journal of Immunology*, 140:3186–3193 (May 1, 1988).

Kast et al., "Protection against lethal Sendai virus infection by in vivo priming of virus–specific cyto–toxic T Lymphocytes with a free synthetic peptide," *Proc. Natl. Acad. Sci. USA*, 88:2283–2287 (Mar. 1991).

Knight et al., "Non–adherent, low–density cells from human peripheral blood contain dendritic cells and monocytes, both with veiled morphology," *Immunology*, 57:595–603 (1986).

Levine et al., "The p53 tumour suprressor gene," Nature, 351:453–456 (Jun. 6, 1991).

Levine, "Tumor Suprressor Genes," *BioEssays*, 12:60–66 (Feb. 1990).

Lie et al., "Peptide Ligand–Induced Conformation and Surface Expression of the L$^d$ class I MHC Molecule," *Nature*, 344:439–441 (Mar. 29, 1990.)

Lotze et al., "Mechanisms of Immunologic Antitumor Therapy: Lessons from the Laboratory and Clinical Applications," *Human Immunology*, 28:198–207 (1990).

Macatonia et al., "Primary Stimulation by Dendritic Cells Induces Antiviral Proliferative and Cytotoxic T Cell Responses In Vitro," *J. Exp. Med.*, 169:1255–1264 (Apr. 1989).

Margalit et al., "Prediction of Immunodominant Helper T Cell Antigenic Sites from the Primary Sequence," *The Journal of Immunology*, 138:2213–2229 (Apr. 1, 1987).

Margulies et al., Expression of H–2D$^d$ and H–2L$^d$ Mouse Major Histocompatability Antigen Genes in L Cells after DNA–Mediated Gene Transer, *The Journal of Immunology*, 130:463–470 (Jan. 1983).

Matis et al., "Clonal Analysis of the Major Histocompatibility Complex Restriction and the Fine Specificity of Antigen Recognition in the T cell . . . ," *The Journal of Immunology*, 130:1527–1535 (Apr. 1983).

Matsumura et al.,"Emerging Principles for the Recognition of Peptide Antigens by MHC Class I Molecules," *Science*, 257:927–934 (Aug. 14, 1992).

Mitsudomi et al., "p53 Gene Mutations in Non–Small–Cell Lung Cancer Cell Lines and Their Correlation with the Presence of ras Mutations and Clinical Features," *Oncogene*, 7:171–180 (Jan. 1992).

Monaco, "A Molecular Model of MHC Class–I–Restricted Antigen Processing," *Immunology Today*, 13:173–179 (1992).

Palker et al., "Type–Specific Neutralization of the Human Immunodeficiency Virus with Antibodies to env–Encoded Synthetic Peptides," *Proc. Natl. Acad. Sci. USA*, 85:1932–1936 (Mar. 1988).

Peace et al., "T Cell Recognition of Transforming Proteins Encoded by Mutated ras Proto–Oncogenes," *The Journal of Immunology*, 146:2059–2065 (Mar. 15, 1991).

Reddehase et al., "A Pentapeptide as Minimal Antigenic Determinant for MHC Class I–Restricted T Lymphocytes," *Nature*, 337:651–653 (Feb. 1989).

Robinson et al., "Antibody–Dependent Enhancement of Human Immunodeficiency Virus Type 1 (HIV–1) Infection in vitro by Serum from HIV–1–Infected and . . . ," *Proc. Natl. Acad. Sci. USA*, 86:4710–4714 (Jun. 1989).

Robinson et al., "Human Monoclonal Antibodies to the Human Immunodeficiency Virus Type 1 (HIV–1) Transmembrane Glycoprotein . . . ," *Proc. Natl. Acad. Sci. USA*, 87:3185–3189 (Apr. 1990).

Romero et al., "H–2K$^d$–restricted Antigenic Peptides Share a Simple Binding Motif," *J. Exp. Med.*, 174:603–612 (Sep. 1991).

Rosenberg, "Lymphokine–Activated Killer Cells: A New Approach to Immunotherapy of Cancer," *JNCI*, 75:595–603 (Oct. 1985).

Rosenberg et al., "Use of Tumor–Infiltrating Lymphocytes and Interleukin–2 In The Immunotherapy of Patients with Metastatic Melanoma," *The New England Journal of Medicine*, 1676–1680 (Dec. 22, 1988).

Rötzschke et al., "Naturally–Occurring Peptide Antigens Derived from the MHC Class–I–Restricted Processing Pathway," *Immunology Today*, 12:447–455 (1991).

Rusche et al., "Antibodies That Inhibit Fusion of Human Immunodeficiency Virus–Infected Cells Bind a 24–Amino Acid Sequence of the Viral Envelope, gp120," *Proc. Natl. Acad. Sci. USA*, 85:3198–3202 (May 1988).

Sarmiento et al., "IgG or IgM Monoclonal Antibodies Reactive with Different Determinants on the Molecular Complex Bearing LYT 2 Antigen Block T Cell–Mediated . . . ," *J. of Immunol.*, 125:2665–2672 (Dec. 1980).

Schulz et al., "Peptide–Induced Antiviral Protection by Cytotoxic T Cells," *Proc. Natl. Acad. Sci. USA*, 88:991–993 (Feb. 1991).

Schumacher et al., "Peptide Selection by MHC Class I Molecules," *Nature*, 350:703–706 (Apr. 25, 1991).

Shirai et al., "Broad Recognition of Cytotoxic T Cell Epitopes from the HIV–1 Envelope Protein with Multiple Class I Histocompatibility Molecules," *The Journal of Immunology*, 148:1657–1667 (Mar. 15, 1992).

Silver et al., "Atomic Structure of a Human MHC Molecule Presenting an Influenza Virus Peptide," *Nature*, 360:367–369 (Nov. 26, 1992).

Singer et al., "Recognition Requirements for the Activation, Differentiation and Function of T–Helper Cells Specific for Class I MHC Alloantigens," *Immunological Reviews*, No. 98:143–170 (1987).

Staerz et al., "Cytotoxic T Lymphocytes Against a Soluble Protein," *Nature*, 329:449–451 (Oct. 1, 1987).

Steinman et al., "Identification of a Novel Cell Type in Peripheral Lymphoid Organs of Mice," *J. Exp. Med.*, 149:1–16 (Jan. 1979).

Stewart et al., *Solid Phase Peptide Synthesis*, Second Edition, Pierce Chemical Company.

Takahashi et al., "An Immunodominant Class I–Restricted Cytotoxic T Lymphocyte Determinant of Human Immunodeficiency Virus Type 1 Induces CD4 . . . ," *J. Exp. Med.*, 171:571–576 (Feb. 1990).

Takahashi et al., "An Immunodominant Epitope of the Human Immunodeficiency Virus Envelope Glycoprotein gp160 Recognized by Class I major . . . ," *Proc. Natl. Acad. Sci. USA*, 85:3105–3109 (May 1988).

Takahashi et al., "Induction of CDB+ Cytotoxic T Cells by Immunization with Purified HIV–1 Envelope Protein in ISCOMs," *Nature*, 344:873–875 (Apr. 26, 1990).

Takahashi et al., "p53: A Frequent Target for Genetic Abnormalities in Lung Cancer," *Science*, 246: 491–494 (Oct. 27, 1989).

Takahashi et al., "Structural Requirements for Class I MHC Molecule–Mediated Antigen Presentation and Cyto–Toxic T Cell Recognition of an Immunodominant . . . ," *J. Exp. Med.*, 170:2023–2035 (Dec. 1989).

Takeda et al., "Antibody–Enhanced Infection by HIV–1 via Fc Receptor–Mediated Entry," *Science*, 242:580–583 (Oct. 28, 1988).

Tam et al., "$S_N2$ Deprotection of Synthetic Peptides with a Low Concentration of HF in Dimethyl Sulfide: Evidence and Application in Peptide . . . ," *J. Am. Chem. Soc.*, 105:6442–6455 (1983).

Townsend et al., "Antigen Recognition by Class I–Restricted T Lymphocytes," *Am. Rev. Immunol.*, 7:601–624 (1989).

Townsend et al., "The Epitopes of Influenza Nucleoprotein Recognized by Cytotoxic T Lymphocytes Can be Defined with Short Synthetic Peptides," *Cell*, 44:959–968 (Mar. 28, 1986).

Tsomides et al., "An Optimal Viral Peptide Recognized by CD8+ T Cells Binds Very Tightly to the Restricting Class I Major Histocompatibility Complex . . . ," *Proc. Natl. Acad. Sci. USA*, 88:11276–11280 (Dec. 1991).

Vogelstein, "A deadly inheritance," *Nature*, 348:681–682 (Dec. 20/27, 1990).

Wilde et al., "Evidence Implicating L3T4 in Class II MHC Antigen Reactivity: Monoclonal Antibody GK 1.5 (Anti–L3T4a) Blocks Class II MHC . . . ," *The Journal of Immunology*, 131:2178–2183 (Nov. 1983).

Winter et al., "Development of Antibodies against p53 in Lung Cancer Patients Appears to be Dependent on the Type of p53 Mutation," *Cancer Research*, 52:4168–4174 (Aug. 1, 1992).

Delattre et al., 1992, "Gene fusion with an ETS DNA–binding domain caused by chromosome translocation in human tumors" *Nature* 359:162–165.

Wildner et al., 1997, "Database screening for molecular mimicry", Immunol. Today 18:252.

Baum et al., 1997, "Also", Immunol. Today 18:252–253.

Del Val et al., 1991, "Efficient processing of an antigenic sequence for presentation by MHC class I molecules depends on its neighboring residues in the protein", Cell 66:1145–1153.

Eisenlohr et al., 1992, "Flanking sequences influence the presentation of an endogenously synthesized peptide to cytotoxic T lymphocytes", J. Exp. Med. 175:481–487.

Bollinger et al., 1996, AIDS 10:S85–S96.

Cohen et al., 1994, Science 260:937–944.

Lanzavecchia, 1993, Science 260:937–944.

Delattre et al. (1992) Nature 359:162–165.

Shapiro et al. (1993) Cancer Research 53:5108–5112.

Galili et al. (1993) Nature Genetics 5:230–235.

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
          (A) LENGTH: 21 amino acids
          (B) TYPE: amino acid
          (D) TOPOLOGY: linear (ii) MOLECULE TYPE: peptide (xi) SEQUENCE DESCRIPTION: SEQ ID NO:1:

Thr Tyr Ser Pro Ala Leu Asn Lys Met Phe Tyr Gln Leu Ala Lys Thr
 1               5                  10                  15

Cys Pro Val Gln Leu
            20

(2) INFORMATION FOR SEQ ID NO:2:

(i) SEQUENCE CHARACTERISTICS:
          (A) LENGTH: 13 amino acids
          (B) TYPE: amino acid
          (D) TOPOLOGY: linear (ii) MOLECULE TYPE: peptide (xi) SEQUENCE DESCRIPTION: SEQ ID NO:2:

Thr Tyr Ser Pro Ala Leu Asn Lys Met Phe Tyr Gln Leu
 1               5                  10

(2) INFORMATION FOR SEQ ID NO:3:

(i) SEQUENCE CHARACTERISTICS:
          (A) LENGTH: 12 amino acids
          (B) TYPE: amino acid
          (D) TOPOLOGY: linear (ii) MOLECULE TYPE: peptide (xi) SEQUENCE DESCRIPTION: SEQ ID NO:3:

Ala Leu Asn Lys Met Phe Tyr Gln Leu Ala Lys Thr
 1               5                  10

(2) INFORMATION FOR SEQ ID NO:4:

(i) SEQUENCE CHARACTERISTICS:
          (A) LENGTH: 14 amino acids
          (B) TYPE: amino acid
          (D) TOPOLOGY: linear (ii) MOLECULE TYPE: peptide (xi) SEQUENCE DESCRIPTION: SEQ ID NO:4:

Lys Met Phe Tyr Gln Leu Ala Lys Thr Cys Pro Val Gln Leu
 1               5                  10

(2) INFORMATION FOR SEQ ID NO:5:

(i) SEQUENCE CHARACTERISTICS:
          (A) LENGTH: 10 amino acids
          (B) TYPE: amino acid
          (D) TOPOLOGY: linear (ii) MOLECULE TYPE: peptide (xi) SEQUENCE DESCRIPTION: SEQ ID NO:5:

```
Phe Tyr Gln Leu Ala Lys Thr Cys Pro Val
 1               5                  10
```

(2) INFORMATION FOR SEQ ID NO:6:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:6:

```
Ser Ser Ser Tyr Gly Gln Gln Asn Pro Ser Tyr Asp Ser Val Arg Arg
 1               5                  10                  15
Gly Ala
```

(2) INFORMATION FOR SEQ ID NO:7:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:7:

```
Ser Ser Ser Tyr Gly Gln Gln Ser Ser Leu Leu Ala Tyr Asn Thr
 1               5                  10                  15
```

(2) INFORMATION FOR SEQ ID NO:8:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:8:

```
Ser Ser Ser Tyr Gly Gln Gln Ser Pro Pro Leu Gly Gly Ala Gln Thr
 1               5                  10                  15
Ile
```

(2) INFORMATION FOR SEQ ID NO:9:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:9:

```
Ser Ser Ser Tyr Gly Gln Gln Asn Pro Tyr Gln Ile Leu Gly Pro Thr
 1               5                  10                  15
Ser Ser
```

(2) INFORMATION FOR SEQ ID NO:10:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:10:

Thr Ile Gly Asn Gly Leu Ser Pro Gln Asn Ser Ile Arg His Asn Leu
1               5                   10                  15
Ser Leu

PEPTIDES CONTAINING A FUSION JOINT OF A CHIMERIC PROTEIN ENCODED BY DNA SPANNING A TUMOR-ASSOCIATED CHROMOSOMAL TRANSLOCATION AND THEIR USE AS IMMUNOGENS

RELATED APPLICATIONS

The present application is a Continuation-In-Part of Ser. No. 08/424,573, filed Apr. 17, 1995, which in turn is a Continuation Application of Ser. No. 08/031,494, filed Mar. 15, 1993, now abandoned.

TECHNICAL FIELD

The present invention pertains to novel immunotherapeutic methods and vaccines, which utilize irradiated, peptide-pulsed antigen presenting cells (APCs) to elicit an immune response in a patient.

BACKGROUND ART

For many viruses, the greatest anti-viral immunity arises from natural infection, and this immunity has best been mimicked by live attenuated virus vaccines. However, in the case of HIV, such live attenuated organisms may be considered too risky for uninfected human recipients because such retroviruses have the potential risks of integrating viral genome into the host cellular chromosomes and of inducing immune disorders. To reduce these risks, an alternative is to use pure, well-characterized proteins or synthetic peptides that contain immunodominant determinants for both humoral and cellular immunity. An important component of cellular immunity consists of class I MHC restriction $CD8^+$ cytotoxic T lymphocytes (CTL) that kill virus infected cells and are thought to be major effectors for preventing viral infection.

Cellular immunity is also a key component of the mechanism of tumor rejection. No previous cancer vaccine has shown much success in treating cancer. Most previous cancer vaccines that have been tried have involved whole cancer cells or cell extracts, which are poorly defined mixtures of many proteins. Prior methods to induce $CD8^+$ CTL with synthetic peptides have been limited to antigens from foreign microbial pathogens, such as viruses and bacteria.

Present theories of tumor initiation and progression hold that tumor cells arise from mutational events, either inherited or somatic, that occur in a normal cell. These events lead to escape from normal control of proliferation in the cell population which contains the tumorigenic mutation(s). In many instances, mutations resulting in substitution of a single amino acid are sufficient to convert a normal cellular protein into an oncogenic gene product. The normal genes which encode the proteins susceptible to such oncogenic mutation are called "protooncogenes".

Ras is a typical protooncogene. The normal protein product of the ras gene is a GTPase enzyme which is part of the pathway that transduces biochemical signals from cell surface receptors to the nucleus of the cell. Mutations which inhibit or abolish the GTPase activity of ras are oncogenic. For example, the $Ala^{59}$, $Gly^{60}$ and $Gln^{61}$ residue of the ras protooncogene are frequently mutated in human tumors (80).

Previous methods for producing $CD8^+$ CTL have not shown the feasibility of inducing CTL against proteins that differ from the normal, "self" proteins by only a single amino acid substitution. However, it is clear from studies of tumor-infiltrating lymphocytes in humans, as well as from animal model studies, that $CD8^+$ CTL can eradicate cancers in vivo.

No previous studies have shown the ability to immunize with a mutant synthetic peptide from a natural endogenous cellular protooncogene product to induce $CD8^+$ cytotoxic T lymphocytes (CTL) that can kill tumor cells expressing a mutant endogenous gene product. Several studies have shown the ability to immunize mice with peptides to induce virus-specific or bacterial-specific CTL (P. Aichele et al (69); M. Schulz et al (42); W. Kast et al (41); J. Harty and M. J. Bevan, J. (77); M. K. Hart et al (79), but with the exception of Harty and Bevan, these have all required the use of adjuvants and high doses of peptide. Furthermore, since viral or bacterial proteins are foreign to the host, and it is known that it is possible to raise CTL to these, it was expected that any viral peptide immunization that succeeded would result in CTL that could kill cells expressing the foreign viral protein.

However, for oncogene products, or products of mutated tumor suppressor genes, for example p53, which reside primarily in the nucleus, it was not clear whether the mutant protein would be produced in sufficient amounts in tumor cells. Nor was it known if the protein would be processed through the appropriate cytoplasmic pathway to be presented by class I MHC molecules to CTL. It had also been questioned whether a single point mutation in a normal, endogenous protein would be sufficient to produce a CTL response.

SUMMARY OF THE INVENTION

The present invention is concerned with providing novel immunoprophylactic or immunotherapeutic methods for use in mammals, preferably humans, which methods are based solely or partially on immunizing said mammal with synthetic or recombinant peptides to induce cytotoxic T lymphocytes. The methods are advantageously applicable to the prevention or treatment of viral infections or cancer(s) in said mammals, since cytotoxic T lymphocytes may be the primary means of host defense against viruses and cancer cells.

Although some CTL have been identified in tumor-infiltrating lymphocytes, their target antigens have remained a mystery. Recent results show that many tumors develop mutations in normal cellular proteins involved in regulating cell growth, but it has not yet been possible to determine whether such mutant cellular proteins will serve as targets for CTL. We have now developed a method to immunize with synthetic peptide corresponding to the site of the mutation in the tumor suppressor gene product, p53, to induce CTL that will kill tumor cells endogenously expressing the mutant p53 gene, present in a large fraction of lung, breast, and colon cancers, as well as other types of cancers.

Our results show that indeed mutant p53, which is found in a large fraction of cancers of the lung, breast, and colon, and other organs, is a good target for $CD8^+$ CTL and that a peptide spanning a single point mutation can be used to immunize an animal to elicit such CTL. We also use a novel method of peptide coated onto syngeneic or autologous myeloid or lymphoid cells, including dendritic cells, which allows the use of very small quantities of peptide for immunization, and which avoids the use of adjuvants, which may be harmful.

Additional results show that peptides having an amino acid sequence that encompass the fusion joint of a tumor-specific fusion protein encoded by a human chromosomal translocation are useful in the method of the invention. Two preferred fusion protein targets for the immunization are created by the translocations t(11;22) (q24;q12) and t(2;3) (q35;q14).

Since only a small fraction of cancers of humans and animals are known to be caused by viruses, most cancers would not be amenable to prevention or treatment by a vaccine aimed at viral proteins. Treatment or prevention would require a vaccine that can target an antigen present in most of the cancers, such as a mutant cellular product. Oncogene and mutant tumor suppressor gene products such as mutant p53, ras, Rb, and brc-abl are present in a very large fraction of cancers. The spectrum of genetic changes which are found in cancer cells is large and growing. Interestingly, many tumors of a particular tissue are often found to contain mutations in many of the same genes. For instance, Vogelstein, Fearon and others (reviewed in ref. 81) have described a number of particular mutations which accumulate during initiation and progression of colon cancer. Similarly, in our laboratory, we have found that mutations in a small number of key growth control genes are often found to occur together in small cell lung carcinomas (82). Such findings suggest that the number of genes which would have to be screened for mutations in a tumor biopsy sample would be finite, and might be quite small.

Thus, the present invention provides a broadly applicable method of immunizing with a safe, non-toxic synthetic peptide, in the absence of harmful adjuvants or live viral vectors, to induce CTL that can specifically lyse tumor cells.

Exemplary of the immunoprophylactic and immunotherapeutic methods encompassed by the present invention are those which comprise a method for eliciting tumor-specific CD8$^+$ cytotoxic T lymphocytes in a human or other mammal, comprising the steps of (1) determining the nucleotide sequence of p53 and/or other protooncogene, tumor suppressor gene or tumor promoter genes in nucleic acid from a tumor sample to identify mutations in a protein-coding region, (2) selecting a synthetic peptide corresponding to the site of mutation in a cellular protooncogene product or tumor suppressor gene product, (3) coating an autologous or syngeneic lymphoid or myeloid cell population containing antigen presenting cells, preferably containing dendritic cells, with the synthetic peptide by incubation with the peptide in vitro, (4) irradiating the cells with between 1,000 and 3,300 rad gamma irradiation, and (5) injecting said peptide-coated cells intravenously into the recipient person or other mammal.

Vaccines encompassed by the present invention are those containing an autologous or syngeneic myeloid or lymphoid cell population coated with a synthetic peptide, in combination with a pharmaceutically acceptable carrier. Preferable vaccines encompassed by the present invention are those prepared as follows:
(1) sequencing of nucleic acid from a tumor sample to identify point mutations,
(2) selecting a synthetic peptide corresponding to the site of a point mutation in a cellular oncogene product or tumor suppressor gene product,
(3) coating an autologous or syngeneic myeloid or lymphoid cell population, which contains antigen presenting cells, preferably containing dendritic cells, with the synthetic peptide by incubation with the peptide in vitro for several hours,
(4) irradiating the cells with between 1,000 and 3,300 rad gamma irradiation, and
(5) combining with a pharmaceutically acceptable carrier.

Additional preferable vaccines encompassed by the present invention are those prepared as follows:

(1) sequencing of nucleic acid from a tumor sample to identify chromosomal translocation mutations,
(2) selecting a synthetic peptide corresponding to the site of a "breakpoint" fusion joint of a fusion protein product encoded by the chromosomal translocation;
(3) coating an autologous or syngeneic myeloid or lymphoid cell population which contains antigen presenting cells, preferably containing dendritic cells, with the synthetic peptide by incubation with the peptide in vitro for several hours,
(4) irradiating the cells with between 1,000 and 3,300 rad gamma irradiation, and
(5) combining with a pharmaceutically acceptable carrier.

BRIEF DESCRIPTION OF THE DRAWINGS

FIG. 1A: BALB/c (H-2$^d$) mice were immunized intravenously with 20×10$^6$ spleen cells pulsed with 0 or 0.01 $\mu$M T1272 peptide for 2 hours at 37° C. and irradiated at 2000 rad. Spleen cells were restimulated with 1 $\mu$M T1272 peptide for 6 days. Cytolytic activity of the restimulated cells was measured with the $^{51}$Cr-labeled BALB/c 3T3 fibroblast targets (18 neo) (21) incubated with 0 or 1 $\mu$M T1272 peptide. FIG. 1B: BALB/c mice were immunized as in A (except spleen cells were pulsed with 10 $\mu$M T1272 peptide), and the immune spleen cells restimulated with 0.1 $\mu$M T1272 or with no peptide. FIG. 1C: To determine the peptide concentration required for sensitizing targets, $^{51}$Cr-labeled BALB/c 3T3 fibroblasts were tested for lysis by T1272 peptide-immune splenic CTL at 40:1 in the presence of varying concentrations of T1272 peptide or P18IIIB peptide from the HIV envelope, which is also presented by a BALB/c class I MHC molecule (21), as a specificity control. Effectors were from mice immunized with cells pulsed with 10 $\mu$M peptide and were restimulated with 0.1 $\mu$M peptide.

FIG. 3A: Splenic CTL from T1272 peptide-immune BALE/c mice (immunized with 10 $\mu$M T1272 peptide-pulsed spleen cells, and stimulated with 0.1 $\mu$M T1272 peptide) were tested against targets, BALB/c 3T3 fibroblasts transfected with neo alone (18 neo) and T1272 transfectant-5 (BALB/c 3T3 fibroblasts transfected with the mutant p53 T1272 gene and the neomycin resistance gene). The 18 neo targets were also tested in the presence of 0.1 $\mu$M T1272 peptide as a lysability control. FIG. 3B: Four T1272 transfectants were tested for recognition by specific splenic CTL from (10 $\mu$M) T1272 peptide-immune BALB/c mice (restimulated with 0.1 $\mu$M peptide): transfectant-5 transfected with mutant T1272 p53 and neo, and transfectants-2, -3, and -4, transfected with ras as well as the mutant T1272 p53 gene and neo. The steady state levels of mutant p53 protein expression in these transfectants were 0.18, 0.15, 0.14, and 0.09 ng p53/mg protein, respectively. All target cells in panel B, including the controls, were grown for three days prior to use in 5 ng/ml mouse recombinant interferon-gamma (Genzyme, Cambridge, Mass.) to optimize MHC expression. FIG. 3C: As a specificity control, a BALB/c 3T3 fibroblast transfectant expressing comparable levels (0.19 ng p53/mg protein) of a different mutant human p53, T104 (24), was used as a target for comparison with the T1272 transfectant-5 described above. Both of these and the control BALB/c 3T3 fibroblast targets (18 neo) were also transfected with the neo gene as a selection marker. The effectors were splenic CTL from (10 μM) T1272 peptide-immune BALB/c mice (restimulated with 0.1 μM peptide).

FIG. 13A shows CTL restimulated with 10 μM PAX-3/FKHR peptide; ○, CT26P/F clone 8; ●, CT26 P/F clone 9; ∇ CT26 with peptide; ▼ CT26 without peptide. FIG. 13B shows CTL restimulated with 1 μM PAX-3/FKHR peptide; ○, CT26P/F clone 8; ●, CT26 P/F clone 9 ; ∇ CT26 with peptide; ▼ CT26 without peptide.

DETAILED DESCRIPTION OF THE INVENTION

Figure 1A:
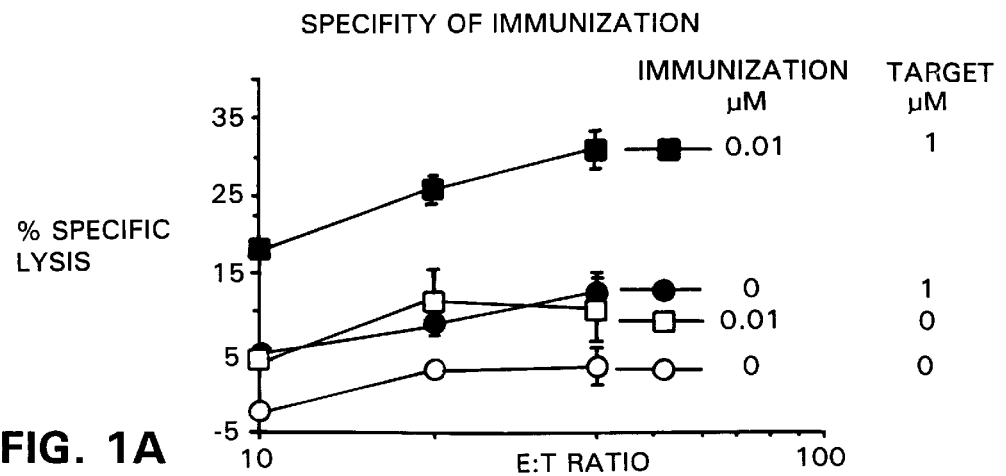
FIGS. 1A–1C are line graphs showing the specificity of induction and of effector function of CTL elicited by peptide-pulsed spleen cells.

The invention comprises a method of immunization for therapeutic or prophylactic purposes and also vaccines to be employed in the immunization method. In particular, the immunogen is made up of antigen-presenting cells which have been coated with peptides that bind to class I MHC molecules on the surface of the antigen-presenting cells. The peptides can be from any source that is distinguishable from "self". That is, they can be derived from the proteins of bacterial antigens or viruses, or from the mutated proteins expressed by tumor cells growing within a host.

The peptides to be employed may be obtained by any of the commonly known methods in the art; for example, but not limited to, total organic synthesis. In selecting the peptide(s) to be employed, the practitioner would seek to provide an epitope which is not normally present in the recipient of the peptide-coated cells. For immunization against a virus, it would be expected that any of the proteins made by the virus would be useful as target sequences, as it would be expected that uninfected cells would not make any of the viral proteins. If a vaccine against a tumor cell is desired, one must identify the proteins produced by the tumor cell which are not normally made by the host. To identify proteins which are produced in a tumor cell that are not normally present in the host can be accomplished by several methods, including a comparison by electrophoresis of the total protein profile of the tumor cells and comparing that profile to that of a normal cell of the same tissue. However, it is more convenient to identify mutations in normal cellular proteins that have led to the tumor phenotype. This is accomplished by sequencing of a nucleic acid obtained from a sample of the tumor tissue.

The nucleic acid obtained from a tumor sample is preferably DNA, but RNA can also be used. The nucleic acid can be sequenced by any of the methods well-known in the art. For rapid sequencing of DNA from a known gene region, the polymerase chain reaction (PCR) is commonly used. For designing primers for use in the PCR, the practitioner would preferably choose sequences expected to be 100–300 bases apart in the nucleic acid to be amplified. The separation should be varied considerably, however. Primers are typically about 20 residues in length, but this length can be modified as well-known in the art, in view of the particular sequence to be amplified. Also, the primers should not contain repetitive or self-complementary sequences and should have a G+C content of approximately 50%. A computer program for designing PCR primers is available (OLIGO 4.0 by National Biosciences, Inc., 3650 Annapolis Lane, Plymouth, Mich.).

Preferable mutations which are useful to identify are point mutations that substitute a different amino acid for the normally occurring residue in the normal gene product. However, mutations which provide small insertions, or which result in the fusion of two proteins which are separated in a normal cell are also useful, as the immunizing peptide can be made to represent the portions of the mutant protein which include the "breakpoint" regions.

When choosing the peptide to synthesize, the practitioner should design the sequence so that it is soluble. Also it is desirable that the peptide sequence be one that is easily synthesized, that is, lacks highly reactive side groups. Furthermore, the peptide need not be the minimal peptide that will bind to the MHC protein. That is, the peptide need not be the shortest sequence that is bound by the MHC protein. The radiation dose that is used in the irradiation step is one which is sufficient to inactivate the genomic DNA, preventing proliferation of the coated cells. However, the metabolism of the peptide-coated cells remains intact and so longer peptides can be presented to the cells to be coated and they will properly process them for presentation by the surface MHC molecules.

MODES FOR CARRYING OUT THE INVENTION

EXAMPLE I

A Mutant p53 Tumor Suppressor Protein is a Target For Peptide-Induced $CD8^+$ Cytotoxic T Cells Cell-mediated immune response against tumors is becoming a focus of cancer immunotherapy. Success has already been achieved with lymphokine-activated killer cells (LAK) (1), and tumor-infiltrating lymphocytes (TIL) (2,3). Although TIL appear to be antigen-specific, in most cases it is not yet clear what target antigen they recognize. An alternative approach is to identify a gene product that is mutated in the cancer cell that might serve as a specific antigenic marker for malignant cells. Promising candidates for this purpose are the products of dominant and recessive oncogenes ("tumor suppressor genes"). Recessive oncogenes are commonly mutated in cancer cells; among these, p53 is the most commonly mutated gene in human cancers (4,5). Table 1 presents a partial list of tumor suppressor genes that have been found to be mutated in human cancers.

TABLE 1

| Gene | Chromosome | Tumor/syndrome |
| --- | --- | --- |
| rb | 13q14.1 | retinoblastoma, small cell lung cancer |
| p53 | 17p13 | lung, colon, breast, Li-Fraumeni |
| mcc, apc | 5q21 | colon, familial polyposis, Gardner's |
| dcc | 18q21 | colon |
| wt1 | 11p13 | Wilms tumor |
| nf1 | 17q11.2 | Neurofibromatosis |
| (VHL) | 3p25 | von Hippel-Lindau |
| (MEN2) | 10q, 1p | multiple endocrine neoplasia, type 1 |
| (MEN1) | 11q13 | multiple endocrine neoplasia, type 2 |
| MLM | 9p13–22 | familial melanoma, lung cancer |
| ? | 3p14, 3p21, 3p25 | lung cancer |
| ? | 17q | early onset breast cancer |

Also, some oncogene products are formed by fusion of two proteins which are normally separate entities as a result of chromosomal rearrangements. An example of such a fusion oncogene is the bcr-abl oncogene.

Hence, an element that makes malignant cells different from the normal cells is the presence of a mutated cellular gene product. It has been found that many mutant p53 proteins also can participate in transformation, probably acting in a dominant negative manner (6). We propose, therefore, that eliciting a cytotoxic T-lymphocyte (CTL) immune response to mutated cellular gene products, particularly mutated products of protooncogenes or tumor suppressor genes can give rise to effective tumor therapy.

Because CTL recognize fragments of endogenously synthesized cell proteins brought to the cell surface by class I MHC molecules (7–9), the mutated gene product does not have to be expressed intact on the cell surface to be a target for CTL. A crucial requirement for such an approach is that an intracellular protein such as ras or p53 be broken down, processed, and presented by class I MHC molecules. p53 resides primarily in the nucleus, where it would not be expected to be accessible to the proteolytic machinery in the cytoplasm responsible for loading of class I molecules, so that only newly synthesized p53 molecules not yet transported into the nucleus might be available for processing. Ras, on the other hand, is a protein that is cytoplasmic. Although promising results have been reported using the ras oncogene product as a T-cell antigen (10, 11), data so far have been limited to T-helper responses, and not specific $CD8^+$ CTL recognizing antigen presented by class I MHC molecules.

Here we show that an endogenously synthesized mutant p53 protein from a human lung carcinoma can render cells targets for $CD8^+$ CTL, and that these CTL are specific for the mutation, and can be generated by immunization of mice with a synthetic peptide corresponding to the mutant sequence of p53.

Peptide synthesis. Synthetic peptides 10–21 residues long corresponding to the p53 gene mutation for T1272 were prepared using standard solid-phase peptide synthesis on an Applied Biosystems 430 A peptide synthesizer using disiopropylcarbodiimide-mediated couplings and butyloxycarbonyl (Boc)-protected amino acid derivatives, and hydroxybenzotriazole preactivation coupling glutamine or asparagine (12). Peptides were cleaved from the resin using the low/high hydrogen fluoride (HF) method (13). Peptides were purified to homogeneity by gel filtration and reverse phase HPLC. Composition was confirmed and concentration determined by amino acid analysis, and sequencing where necessary.

CTL generation: BALB/c ($H-2^d$) mice were immunized intravenously with $20\times10^6$ spleen cells pulsed with various concentrations of T1272 peptide for two hours at 37° C. and irradiated at 2,000 rad (by the method of H. Takahashi, Y. Nakagawa, K. Yokomuro, & J. A. Berzofsky, submitted). One week later, immune spleen cells ($3\times10^6$/ml) were restimulated for six days in vitro with various concentrations of T1272 peptide in 10% Rat-T Stim, without Con A (Collaboration Research Incorporated, Bedford, Mass.) in 24-well culture plates in complete T-cell medium (CTM) (14), a 1:1 mixture of RPMI 1640 and Eagle-Hanks amino acid medium containing 10% fetal bovine serum, 2 mM L-glutamine, penicillin (100 U/ml), streptomycin (100 µg/ml), and $5\times10^{-5}$M 2 mer-captoethanol.

CTL Assay. Cytolytic activity of the restimulated cells was measured as described (15) by using a six-hour assay with various $^{51}$Cr-labeled targets. For testing the peptide specificity of CTL, effectors and $^{51}$CR-labeled targets were mixed with various concentrations of peptide at the beginning of the assay. The percentage specific $^{51}$CR release was calculated as 100(experimental release—spontaneous release)/(maximum release—spontaneous release). Maximum release was determined from supernatants of cells that were lysed by addition of 5% Triton X-100. Spontaneous release was determined from target cells incubated without added effector cells.

CTL phenotype determination: Two$\times10^3$ $^{51}$CR-labeled BALB/c 3T3 neo gene transfectants were cultured with cells of the long-term anti-T1272 CTL line at several effector/target cell ratios in the presence of 1 µM peptide T1272. Monoclonal antibodies 2.43 (anti-CD8) (16) (dilution 1:6) and GK1.5 (anti-CD4) (17) (dilution 1:3) were added to the CTL assay. Rat anti-mouse CD4 mono-clonal antibody GK1.5 (17) was provided by R. Hodes (NCI). Rat anti-mouse CD8 monoclonal antibody 2.43 (16) was provided by R. Germain (NIAID).

MHC-restriction mapping. L-cell ($H-2^k$) transfectants expressing $D^d$ (T4.8.3 (18), $L^d$ (T1.1.1 (19) and $K^d$ (B4III-2(20)) were used as targets, in the presence or absence of 0.1 µM peptide T1272. neo gene transfected BALB/c 3T3 fibroblasts (18 neo) ($H-2^d$) (21) were used as a positive control, and neo gene-transfected L-cells L28 ($H-2^k$) (21) were used as a negative target control, also in the presence or absence of peptide.

Construction of expression vectors. The full open reading frame (ORF) for the mutant p53 was cloned into the pRC/CMV expression vector (Invitrogen, San Diego, Calif.) for endogenous processing studies. The mutation determination and cloning of the full open reading frame of p53 from tumor T1272 were described previously (22). This clone was derived by PCR amplification of cDNA generated from reverse transcription of tumor RNA, with synthetic EcoRl sites at each end, and cloned into pGEM4 (ProMega, Madison, Wis.). The full open reading frame was sequenced in both directions to exclude artifactual PCR-derived mutations. The clone that was sequenced, however, had lost the 5'EcoRl site in the cloning process. This was reconstructed by cutting with SgrAl which cuts the clone twice, once within p53 5' to the mutation size, and once in the vector just upstream from the defective multi cloning site, excising the defective EcoRl site. Another clone of p53 (T863) which had been sequenced and found to be normal 5' to the SgrAl site and also contained SgrAl fragment from T1272. This reconstructed an open reading frame which could be excised by EcoRl from the pGEM4 vector. EcoRl is not a cloning site that is available in pRC/CMV, however, so the open reading frame was then excised with EcoRl and cloned into the EcoRl site of PGEM7Zf+ (ProMega, Madison, Wis.). A clone with the proper orientation was selected, and the ORF was then excised with HindIII and XbaI, and cloned into those sites in pRC/CMV. The structure was verified by restriction mapping. To generate murine cell lines which stably expressed the entire human T1272 mutant p53 protein, transfectants were made with either human T1272 p53 alone or together with activated H-ras. 10 µg of activated ras expression plasmid (pEJ6.6, ATCC, Rockville, Md.) and 100 µg of sonicated salmon sperm DNA were mixed in 60 µl of TE (10 mM Tris-HCl, 1 mM EDTA pH 8.0) and added to $5\times10^6$ BALB/c 3T3 cells (ATCC, harvested in mid log phase) at room temperature. This mixture was electroporated using a BioRad Gene Pulser (Richmond, Calif.) at 300V and 960 µF in the 0.4 cm cuvette. The entire contents of the cuvette were plated into 7 ml of RPMI 1640 plus 10% Fetal Bovine Serum (FBS) and 5 mM sodium butyrate in a T25 flask. 24 hours later, this flask was split to three-10 cm dishes and grown for 2 weeks in RPMI 1640+ 10% FBS with 500 µg/ml Geneticin (Gibco/BRL, Bethesda, Md.) added to those transformations which did not contain activated ras. Ras containing transfectants were selected by focus formation without Geneticin. BALB/c 3T3 (neo transfected) foci (colonies growing in the presence of Geneticin) were picked and expanded into cell lines. As expected, the p53 plus ras transfectants had a much higher growth rate than cells transfected with p53 and neo alone and selected for neomycin resistance.

All transfectants were tested for p53 expression by both ELISA on whole cell lysates (Oncogene Science, Uniondale, N.Y., used according to the manufacturer's instructions) and immunoblot with Ab-2 (Oncogene Science) as previously described (23).

Analysis of mutations and initial selection of peptides. Over 100 p53 mutations from lung cancers have been characterized in our lab (22,24–26). All of the tumors used for these studies were collected from patients on clinical protocols at the National Cancer Institute/Navy Medical Oncology Branch or through Lung Cancer Study Group protocols. The tumor T1272 (22) was derived from a patient with adenocarcinoma of the lung entered on Lung Cancer Study Group protocol 871.

To show that point mutations in the p53 tumor suppressor gene create neo-antigenic determinants which can serve as tumor antigens when processed and presented by class I MHC molecules, we examined a point mutation occurring in a human lung carcinoma. The mutant p53 gene of non-small-cell lung cancer 1272 had been previously sequenced and found to have a single point mutation of Cys to Tyr at position 135 (22). We also noted that the mutation created a new binding motif sequence (27,28) for the $K^d$ class I MHC molecule by inserting a critical Tyr anchor residue. A 21-residue sequence from residues 125 to 145 (TYSPALNKMFYQLAKTCPVQL(SEQ ID NO:1)) encompassing the point mutation was chosen because it corresponded to a segment predicted to be a potential T-cell antigenic site on the basis of being amphipathic if folded as a helix (29–31). The choice of end points also took into consideration solubility and the preference to avoid more than one Cys residue that might result in crosslinking and solubility problems. A peptide of this sequence was synthesized and dubbed the T1272 peptide, for use in immunization and characterization of the specificity of CTL. It should be noted that this peptide has one difference from the human wild type p53, namely the 135 Cys to Tyr mutation noted, which is also a mutation with respect to the mouse p53. However, it also has two other differences from the mouse wild type p53 at which the human protein differs (129 Ala in the human p53 which is Pro in the mouse, and 133 Met in the human p53 which is Leu in the mouse) (32). Thus, any response to this peptide in the mouse might depend on any one or more of these three differences from the wild type mouse p53 protein. Nevertheless, all three of these are point mutations as far as the mouse is concerned. Thus, for our purposes, a response to any one of these would demonstrate the ability of an endogenous mutant p53 protein to serve as a target antigen for CD8+ CTL.

Figure 1B:
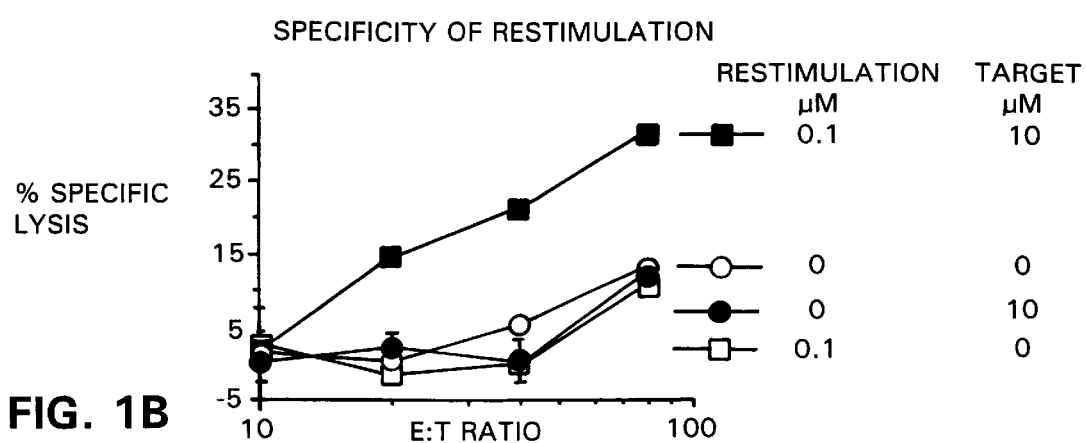
Figure 1C:
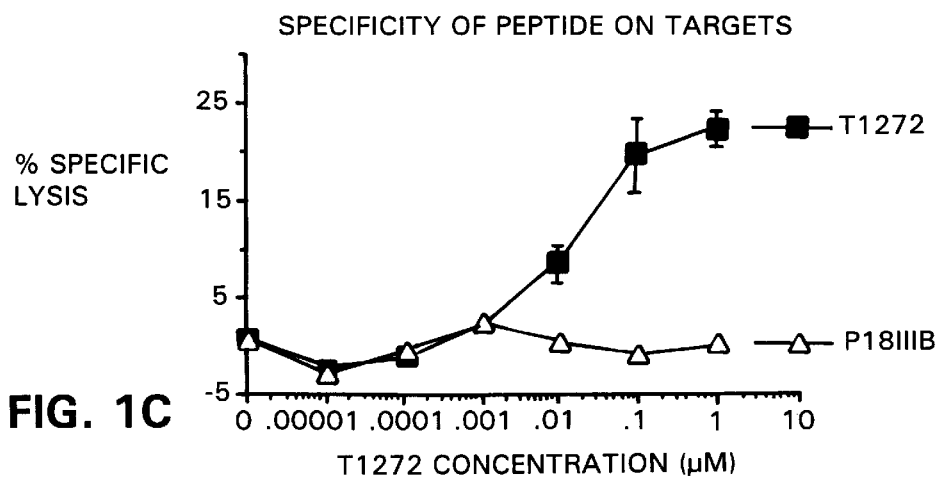

Immunization of BALB/c (H-$2^d$) mice with T1272 peptide-pulsed spleen cells as described herein (Example 2) and restimulation with peptide was used to generate CTL specific for this peptide. Specificity for T1272 was found at three levels—lymphocyte priming, restimulation, and effector function. As a negative control peptide we used p18IIIB from the HIV-1 envelope protein, which can also be presented to CTL by a class I molecule in the same mouse strain (21). Thus, only T1272 peptide-pulsed spleen cells, not non-pulsed control spleen cells, could prime mice for development of CTL able to kill T1272 peptide-sensitized BALB/c 3T3 fibroblast targets ("18 neo"(21), transfected with the neomycin resistance gene as a control for transfection studies; see below (FIG. 1A). Likewise, T1272 peptide was required to restimulate immune T cells in vitro to kill the specific target (T1272 peptide sensitized BALB/c 3T3 (18 neo) fibroblasts) (FIG. 1B). Stimulation with no peptide (FIG. 1B) did not produce CTL activity. At the effector level, CTL from T1272-primed and restimulated spleen cells preferentially killed T1272 sensitized targets and not unpulsed targets (FIGS. 1A and B) or p18IIIB sensitized targets (FIG. 1C). When titrated in the killing assay, the T1272 peptide was able to sensitize targets at concentrations of less 0.1 $\mu$M, whereas the P18IIIB peptide was not recognized at any concentration (FIG. 1C).

Figure 2A:
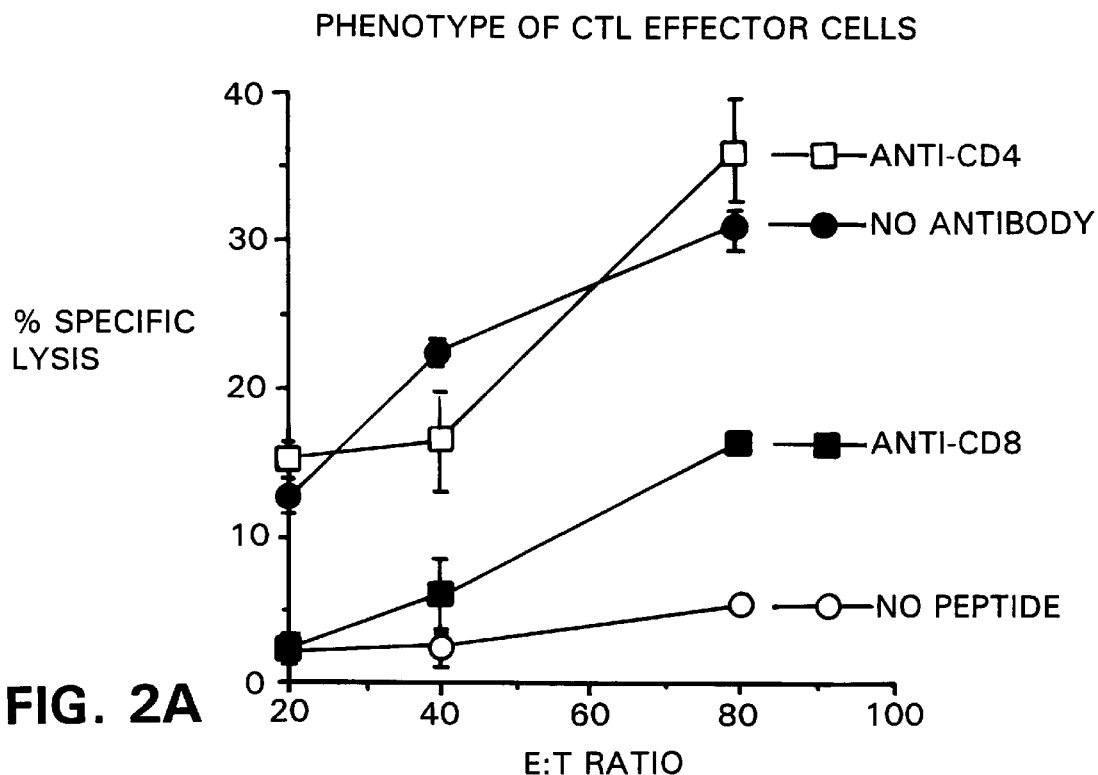
FIG. 2A is a line graph showing the phenotype of the H-2d CTL line specific for peptide T1272-sensitized cells. E/T, effector/target cell.

A long-term line of CTL effectors specific for T1272-peptide was established by repetitive stimulation of spleen cells from peptide-pulsed spleen cell-immunized mice with T1272 peptide and a source of IL-2. Treatment of the CTL effector cells with anti-CD8 blocking mono-clonal antibody 2.43 (16), but not with anti-CD4 blocking antibody GK1.5 (17), led to loss of killing activity on the control fibroblasts incubated in the presence of T1272 peptide (FIG. 2A). In this experiment, 2×10$^3$ $^{51}$Cr-labeled BALB/c 3T3 neo gene transfectants were cultured with cells of the long-term anti-T1272 CTL line at several effector/target cell ratios in the presence of 1 $\mu$M peptide T1272. Monoclonal antibodies 2.43 (anti-CD8) (16) (dilution 1:6) and GK1.5 (anti-CD4) (17) (dilution 1:3) were added to the CTL assay. The control group was untreated.

The result of the experiment shows that the effector cells that recognize and kill peptide-bearing cells in this system are conventional CD8+ CD4− CTL. Beyond simply phenotyping the cells in the population responsible for the killing activity, this experiment also shows that the CD8 molecule plays a functional role in the CTL response, indicative of recognition of antigen presented by class I MHC molecules.

Figure 2B:
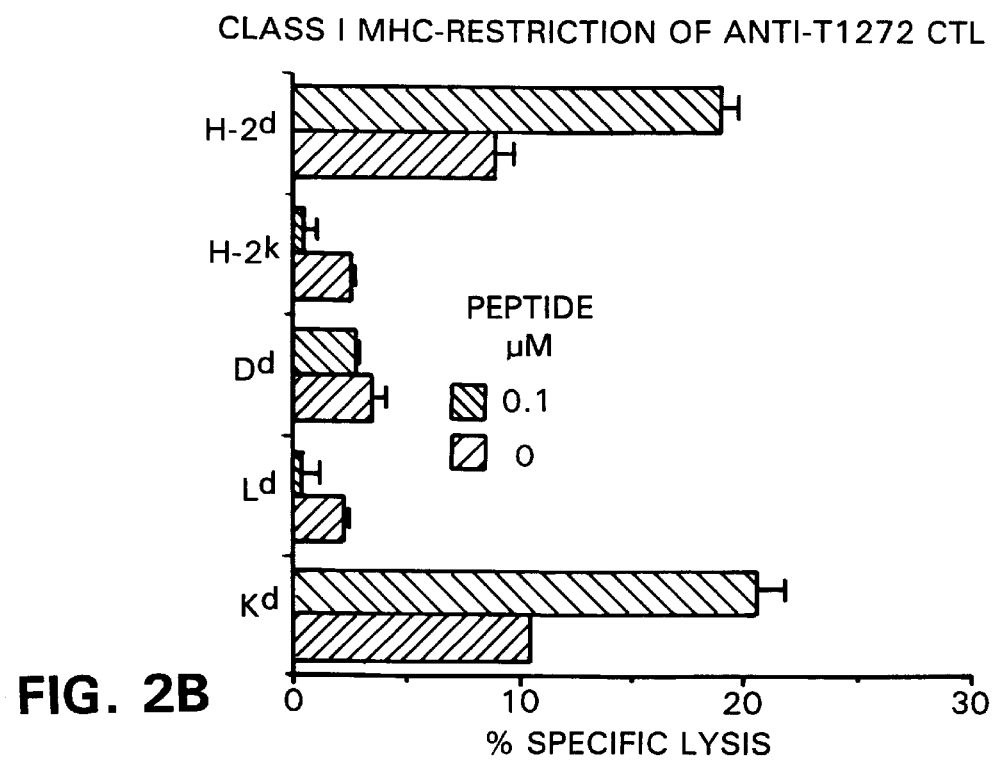
FIG. 2B is a low graph showing that CTL specific for peptide T1272 are restricted by the class I molecule K$^d$.

The BALB/c 3T3 (18 neo) fibroblasts (H-$2^d$) used as targets in these experiments express class I but not class II MHC gene products. Therefore, the T1272-specific CTL capable of lysing the peptide-bearing fibroblasts were likely to be class I MHC molecule-restricted, as is usual for CD8+ effector T cells and is suggested by the anti-CD8 blocking study. To distinguish among the three H-$2^d$ class I molecules of BALB/c, D$^d$, L$^d$, and K$^d$, we used three L-cell (H-$2^k$) transfectants, T4.8.3 (18), T1.1.1 (19), and B4III-2 (20), expressing the D$^d$, L$^d$, and K$^d$ MHC molecules, respectively, and demonstrated that recognition of T1272 peptide is restricted by the class I molecule K$^d$, but not the L$^d$ and D$^d$ molecules (FIG. 2B).

In this experiment, 2×10$^3$ $^{51}$Cr-labeled targets were cultured with T1272-immune splenic effector cells (a short-term line stimulated twice with 0.1 $\mu$M peptide) at several effector/target cell ratios in the presence or absence of 0.1 $\mu$M peptide T1272. L-cell (H-$2^k$) transfectants expressing D$^d$(T4.8.3 (18)), L$^d$ (T1.1.1 (19)) and K$^d$ (B4III-2 (20)) were used as targets. neo gene transfected BALB/c 3T3 fibroblasts (18 neo) (H-$2^d$) (21) were used as a positive control, and neo gene-transfected L-cells L28 (H-$2^k$) (21) were used as a negative target control. Spontaneous release was less than 20% of maximal release. Although background without peptide varied among the different transfectants from experiment to experiment, T1272 peptide-specific lysis was consistently seen only in the cells expressing K$^d$, in five different experiments. L cell fibroblasts expressing only H-$2^k$ served as a negative control. This result is consistent with the creation of a new K$^d$-binding motif (27,28) by the p53 point mutation, as noted above.

To more precisely identify the T-cell epitope recognized by T1272-specific BALB/c CTL, and to test the hypothesis that the response was specific for the neo-antigenic determinant created by the mutation, a series of peptides was synthesized and various concentrations of these peptides were individually added to effectors and $^{51}$Cr-labeled fibroblast targets at the start of the assay culture. We measured the cytotoxic activity of two types of effector cells: spleen cells from mice immunized with peptide-pulsed cells stimulated once in vitro with 0.1 $\mu$M T1272 peptide (presumably polyclonal effector populations), and a short-term CTL line (possibly an oligoclonal population, although only three weeks in culture). Using three overlapping larger fragments 12–14 residues long spanning the whole T1272 sequence, we first mapped the determinant to be within the C-terminal 14 residues of the T1272 peptide. This contained the putative new K$^d$-binding motif (27,28). The mapping to this motif was confirmed by use of a 10-residue peptide, V10, corresponding to this motif, which was found to have higher activity than the whole T1272 peptide (Table 2).

TABLE 2

Mapping of a neoantigenic CTL site in the
T1272 mutant p53 peptide in H-2$^d$

| mice Peptide | Sequence ↓ | | % specific $^{51}$Cr release | |
|---|---|---|---|---|
| | | | Immune spleen cells | CTL line |
| T1272 | TYSP<u>A</u>LNK<u>M</u>FYQLAKTCPVQL | (SEQ ID NO: 1) | 35.4 | 24.7 |
| L13 | TYSP<u>A</u>LNK<u>M</u>FYQL | (SEQ ID NO: 2) | 14.7 | −8.9 |
| T12 | <u>A</u>LNK<u>M</u>FYQLAKT | (SEQ ID NO: 3) | 9.7 | −9.1 |
| L14 | K<u>M</u>FYQLAKTCPVQL | (SEQ ID NO: 4) | 22.2 | 22.1 |
| V10 | FYQLAKTCPV | (SEQ ID NO: 5) | 62.7 | 53.7 |

CTL effectors were spleen cells derived from the 10 μM T1272 peptide-pulsed spleen cell-immunized BALB/c mice (restimulated 6 days with 0.1 μM T1272 peptide) (left) or a short-term T1272-specific BALB/c CTL line (after 3 weeks in culture) (right). BALB/c 3T3 neo-only transfectants (18 neo) (H-2$^d$) plus 0.1 μM synthetic peptide were used as targets with BALB/c spleen effectors or with 1.0 μM peptide for the CTL line. The peptides were titrated over two logs of concentration, and the results shown here are representative. The effector/target cell ratio was 40:1. The arrow and bold-face amino acids indicate the site of the 135 Cys to Tyr mutation. Underlined amino acids correspond to human p53 residues which differ from the mouse p53. Comparable results were obtained in two additional experiments.

Consistent results were found over two logs of peptide concentration (0.01–1 μM), and representative results are shown in Table 2. The K$^d$ motif requires a Tyr at position 2 and an aliphatic amino acid, such as Val, at the C-terminus. Usually the K$^d$-binding motif is 9 residues long, but the presence of a Pro residue presumably allows enough of a bulge to permit the 10-residue peptide to bind, as has been shown in several other systems (33–37). Note also that the optimal 10 residue peptide V10 does not encompass any of the mouse-human differences, so the MHC recognition is not dependent on these other substitutions relative to the mouse sequence which might appear as foreign to the mouse.

Figure 3A:
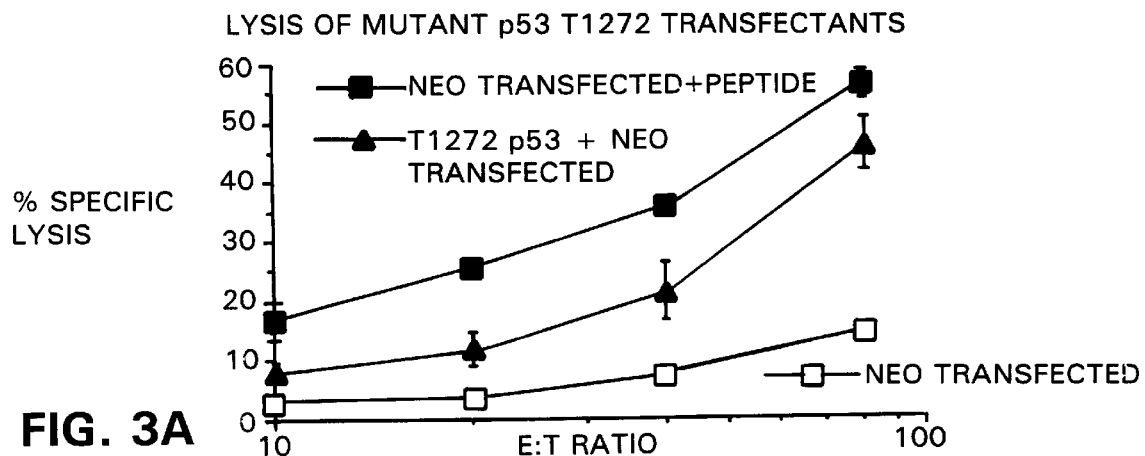
FIGS. 3A–3C are line graphs showing that peptide-induced CTL kill targets endogenously expressing mutant p53.
Figure 3B:
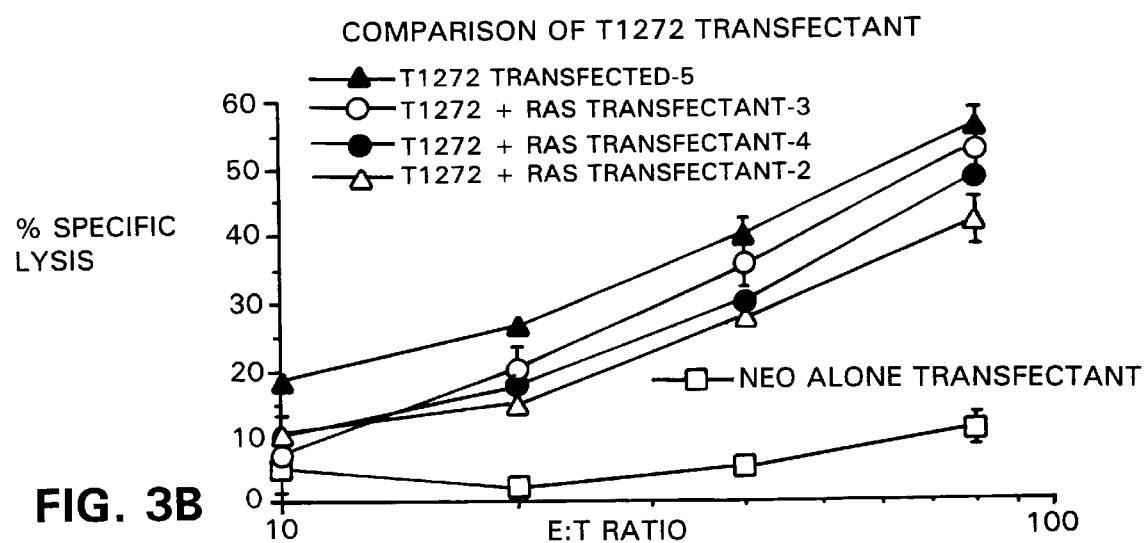
Figure 3C:
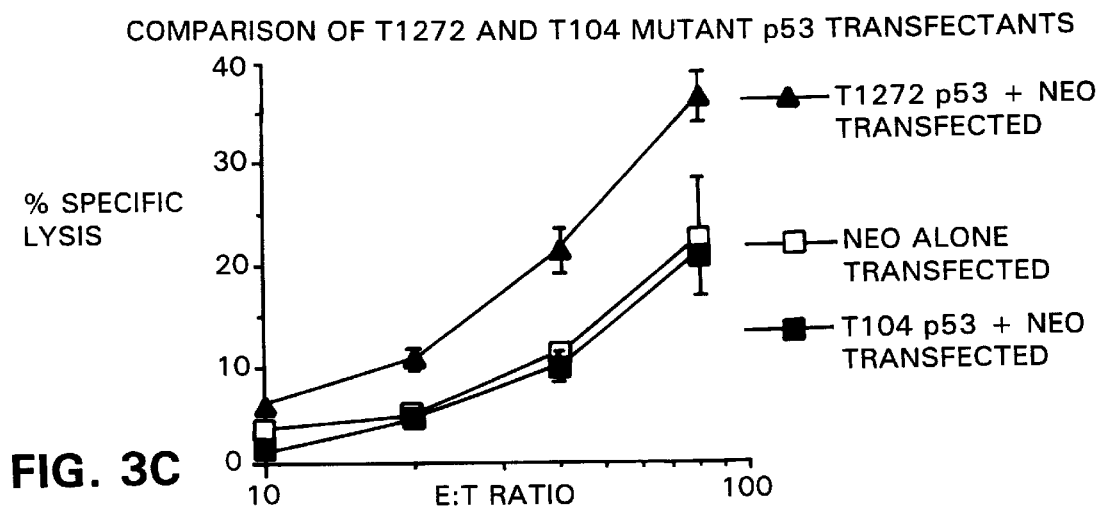

Generation of peptide-specific CTL does not always guarantee that the CTL will kill targets endogenously expressing the protein from which the peptide was derived (38). It is also necessary that the endogenous protein be processed in such a way as to generate the CTL antigenic site, and that the corresponding peptide fragment be transported into the endoplasmic reticulum of the cell and be associated with the relevant MHC class I molecule (7–9). Whereas, in general, cells exposed to exogenous synthetic peptide do not require endogenous processing of antigen (39), transfected cells expressing endogenous antigen generally do (7,40). Therefore, we asked whether the CTL we had generated could also kill targets transfected with and expressing an endogenous mutant T1272 p53. In this case we found that immunization with T1272 peptide-pulsed spleen cells and restimulation with peptide generated CTL that lysed cells expressing an endogenous mutant p53 T1272 gene in the absence of any peptide added, but not control BALB/c 3T3 (18 neo) cells that were transfected only with the neomycin resistance gene (FIG. 3A). The steady-state level of p53 expression by ELISA analysis in this transfectant (0.18 ng/mg protein) is near the low end of the range of mutant p53 levels found in naturally occurring tumors (0.1 to 70 ng/mg protein) In addition to this cell line (T1272 transfectant-5), three other transfectants that were cotransfected with the T1272 mutant p53 gene and ras, were also lysed specifically (FIG. 3B). These latter ras cotransfectants were tumorigenic in BALB/c mice. Finally, as a specificity control, BALB/c 3T3 fibroblasts trans-fected with a different mutant human p53, T104 (with a three base-pair in-frame deletion of codon 239 (24), that has the wild type sequence in the region of the T1272 mutation at codon 135), was not lysed any more than the 18 neo control targets (FIG. 3C). The T104 transfectant expresses a comparable level of mutant human p53 (0.19 ng/mg protein) to that expressed by the T1272 transfectants used in this experiment. This result confirms that the CTL are recognizing a neoantigenic determinant in the mutant p53 protein created by the mutation at position 135, and not just the mouse-human differences. Similar results were obtained in a repeat experiment. Thus, we conclude that mutant p53 is endogenously processed and presented by class I MHC molecules, and is therefore a potentially good target for specific cell-mediated immunity against tumors bearing such p53 mutations.

The use of peptide vaccines in eliciting tumor immunity may have advantages in immunotherapy. In the case of viruses, Kast et al (41) and Schulz et al (42) have been able to achieve protection by immunization with peptides corresponding to CTL antigenic sites of the virus. As for tumors, Chen et al (43) observed protection against a tumor expressing HPV 16 E7 in C3H mice, that was dependent on CD8$^+$ T cells, when those animals were immunized with cells transfected with the E7 gene, but peptides were not studied and the determinant was not mapped. E7 is a viral protein, even though it functions as an oncogene product. Thus, it was not clear that a mutant endocenous cellular oncogene product, in this case a mutant form of the normal cellular tumor suppressor gene p53, could serve as a target for CD8$^+$ CTL, or that a peptide could elicit such immunity. Indeed, because p53 resides primarily in the nucleus, it was not clear if sufficient p53 would be available in the cytoplasm to be processed for presentation by class I MHC molecules. Our own experiments showed that CD8$^+$ CTL recognized mutant p53 T1272 gene-transfected cells as well as T1272 peptide-bearing cells, that these CTL were specific for a neoantigenic determinant created by the oncogenic point mutation, and that these CTL could be generated by peptide immunization.

Rapid methods for sequencing p53 mutations from tumors have been developed (26). It is expected that these methods can easily be used to identify the sequences of other known genes. Thus, it is entirely feasible to sequence the protein coding region of a number of probable genes to search for mutations which are present in the genome of cells from a tumor biopsy sample. In particular, the availability of PCR primers which saturate the protein coding regions of known protooncogenes and tumor suppressor genes, since the DNA sequence of many of these genes are known, allows the rapid determination of the sequence of their gene products from DNA isolated from a biopsy specimen. This technology is well-known in the art. Such sequences determined on biopsy specimens or tumors resected at surgery could be used to design synthetic peptides for immunization for immunotherapy, or after surgery as "adjuvant" immunotherapy. Although immunization with Ewing's sarcoma (ES) and alveolar rhabdomyosarcoma (ARMS) are both small, blue, round cell tumors of childhood that have recently been found to harbor tumor-specific translocations thought to play a role in the pathogenesis of these tumors. To develop new therapeutic approaches to the treatment of these tumors, we have determined that cytotoxic T lymphocytes (CTL) can be generated against peptides derived from the tumor-specific fusion proteins generated by the t(1 1;22) (q24;q12) giving rise to a EWS/FLI-1 chimeric protein in the case of ES or the t(2;13)(q35;q14) giving rise to the PAX-3/FKHR chimeric protein in the case of ARMS (See, Table 3).

TABLE 3

Summary of Translocation Sequences and Predicted Major Histocompatibility Complex Binding Motifs

| Translocation | Peptide Sequence | Human MHC Class I | Human Class II | Mouse I & II |
|---|---|---|---|---|
| EWS/FLI 1 (type 1)[a] | SSSYGQQN/PSYDSVRRGA (SEQ ID NO: 6) | −A3, −A11, −A31, −B53 | −DR (2, 5, 7), −DR3, −DR7, −DR8 | No motifs |
| EWS/FLI 1 (type 2) | SSSYGQ/QSSLLAYNT (SEQ ID NO: 7) | −A2, −A3, −A24, −B62, −C4 | −DPw4, −DR1, −DR3/DRw52, −DR (2, 5, 7), −DR7, −DR4w4, DQ3.1 | H-2 Kd |
| EWS/FLI 1 (type 4) | SSSYGQQ/SPPLGGAQTI (SEQ ID NO: 8) | −A2, −A24, −B35, −B53, −C4 | −DR3, −DR (2, 5, 7), −DR7 | H-2 Kd |
| EWS/FLI 1 (type 8) | SSSYGQQN/PYQILGPTSS (SEQ ID NO: 9) | −A2, −A3, −A11, −A24, −B53 | −DR1, −DR3/Drw52, −DPw4, −DR (2, 5, 7), −DR7 | H-2 Kb, Db |
| PAX-3/FKHR[b] | TIGNGLSPQ/NSIRHNLSL (SEQ ID NO: 10) | −A11, −A33, −A68 (a), −B8, −B53 | −DR1, −DR (2, 5, 7), −DR3, −DR4w4 −DR7 | H-2 Dd, Ld[c] I-EK |

[a]- t (11; 22) (q24:q12) Ewing's Sarcoma (ES)
[b]- t (2; 13) (q35:q14) Alveolar Rhabdomyosarcoma (ARMS)
[c]- no1t0 predicted; determined by restriction autologous peripheral blood cells incubated briefly in peptide and reinfused may be more cumbersome than immunization with an "off-the-shelf" vaccine, as a form of immunotherapy, it certainly requires less effort and expense than in vitro expansion of tumor infiltrating lymphocytes (TIL) for reinfusion, or other similar forms of adoptive cellular immunotherapy. As a preliminary step, one could also determine whether CTL specific for the mutant oncogene peptide already existed in a patient's peripheral blood or tumor-infiltrating lymphocytes. If so, peptide immunization might boost an inadequate response to levels capable of rejecting the tumor, or to a level sufficient for clearing micrometastases after resection of the primary tumor. If not, peptide immunization might still be efficacious, because cells pulsed with high concentrations of the peptide may be more immunogenic than the tumor cell. Once generated, the CTL may recognize low levels of the endogenously processed mutant oncogene product presented by class I MHC molecules on cells of the tumor. Indeed, evidence exists that the requirements for immunogenicity to elicit CTL are greater than the requirements for antigenicity. That is, recognition of an antigen by CTL already elicited by some other type of immunization requires a lower amount of antigen than that required to initially provoke the CTL response (44). The current finding that endogenously expressed p53 can serve as a target antigen for cell lysis by CD8+ CTL generated by peptide immunization lends credibility to this approach to potential vaccine immunotherapy of cancer.

EXAMPLE II

In Vitro Recognition and Lysis of Peptide-Pulsed Tumor Targets by Cytotoxic T Cells Generated by Peptide-Pulsed Spleen Cell Immunization Since CTL recognize fragments of peptides brought to the cell surface by class I MHC molecules during normal degradation processes, a requirement for the success of this approach is that the peptides bind class I MHC molecules. We noted that these fusion proteins generate potential peptides with binding motifs for MHC class I and 11 molecules. To test this, mice were immunized with synthetic peptides spanning the translocation breakpoints. CTL were generated which were capable of specifically recognizing and lysing peptide-pulsed targets in vitro. We have subsequently shown that a mouse colon adenocarcinoma cell line (CT26.W, which does not express either of the EWS/FLI-1 or the PAX-3/FKHR fusion proteins) that has been transfected with a PAX-3/FKHR expression vector can also be recognized and lysed by CTL derived from mice immunized with a synthetic peptide derived from the PAX-3/FKHR fusion protein.

Figure 12:
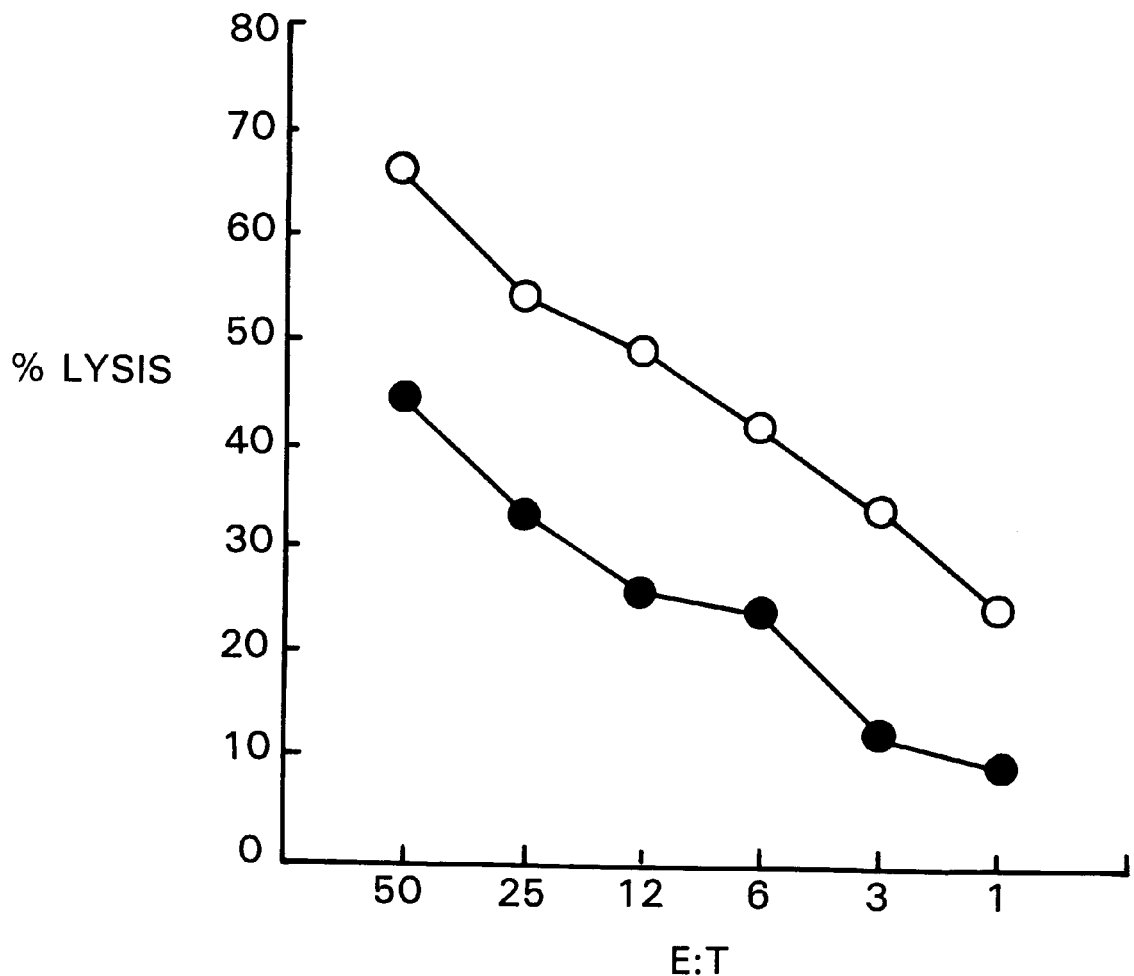
FIG. 12 is a line graph showing recognition of EWS/FLI 1 Type 8 peptide-pulsed EL4 target cells by uEWS/FLI type 8 CTL. At day 5; ○, α EWS/FLI 1 (type 8) CTL stimulated with 20 μM peptide against targets pulsed with 10 μM peptide; ●, α EWS/FLI 1 (type 8) CTL stimulated with 20 μM peptide against targets not exposed to peptide.

In Vitro Recognition and Lysis of Peptide-Pulsed Tumor Targets by aEWS/FLI I Type 8 Cytotoxic T Cells Generated by Peptide-Pulsed Spleen Cell Immunization Specific in vitro recognition and lysis of tumor cell targets was measured using a 6-hr $^{51}$Cr release assay. Briefly, EL4 (H-2$^b$) tumor cells were labeled with 300 $\mu$Ci sodium chromate $^{51}$Cr) and pulsed with 10 $\mu$M EWS/FLI 1 type8 peptide for 2 hr at 37° C. The cells were washed to remove unincorporated $^{51}$Cr and unbound peptide and incubated in the presence of cytotoxic T cells (CTL) generated by peptide-pulsed spleen cell immunization of BALB.B mice at the effector to target cell ratios (E:T) indicated in FIG. 12. CTL were obtained from mice immunized 4 weeks prior to and tested for recognition and lysis 5 days after in vitro restimulation with irradiated sygeneic spleen cells pulsed 2 hr with 20 $\mu$M peptide.

Figure 13A:
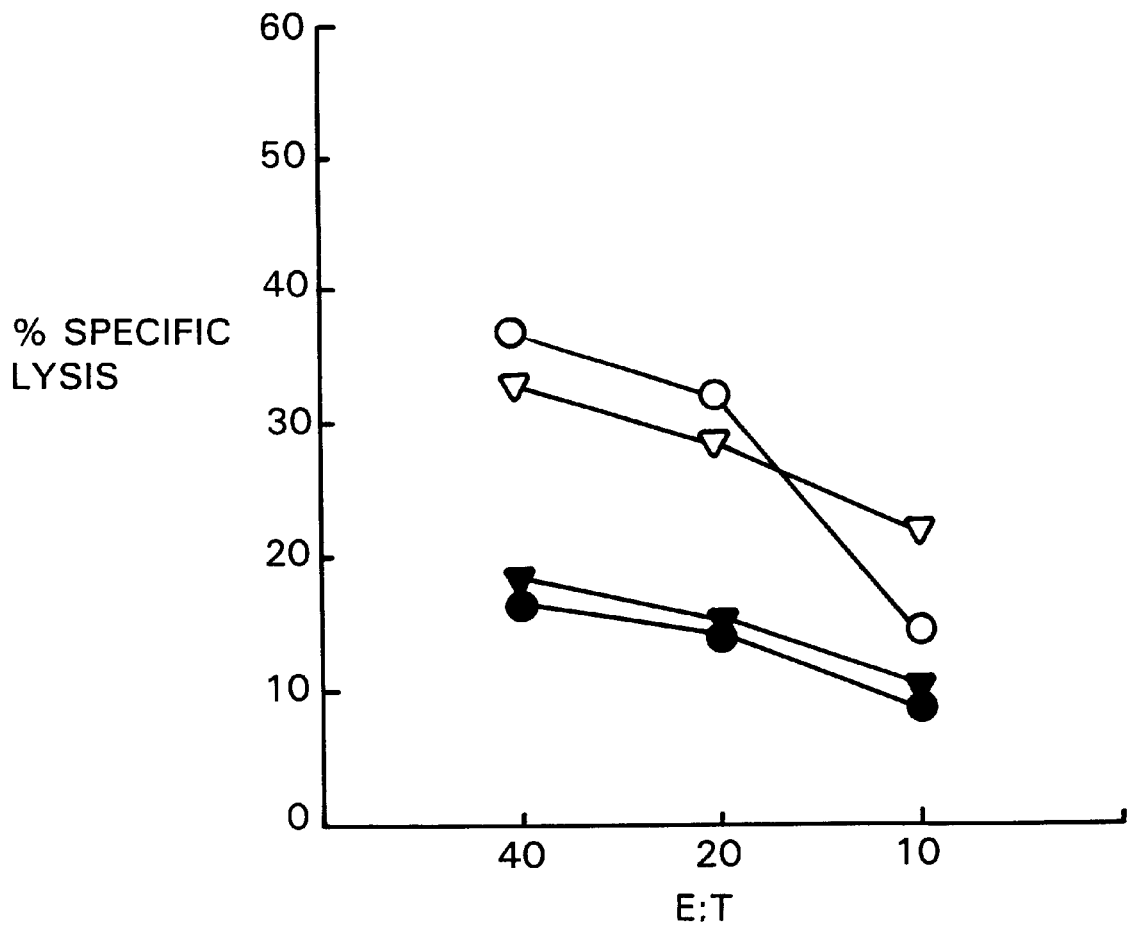
FIGS. 13A and 13B are line graphs showing recognition of peptide-pulsed CT26 and CT26-transfectants by αPAX3/FKHR CTL. At day 5.
Figure 13B:
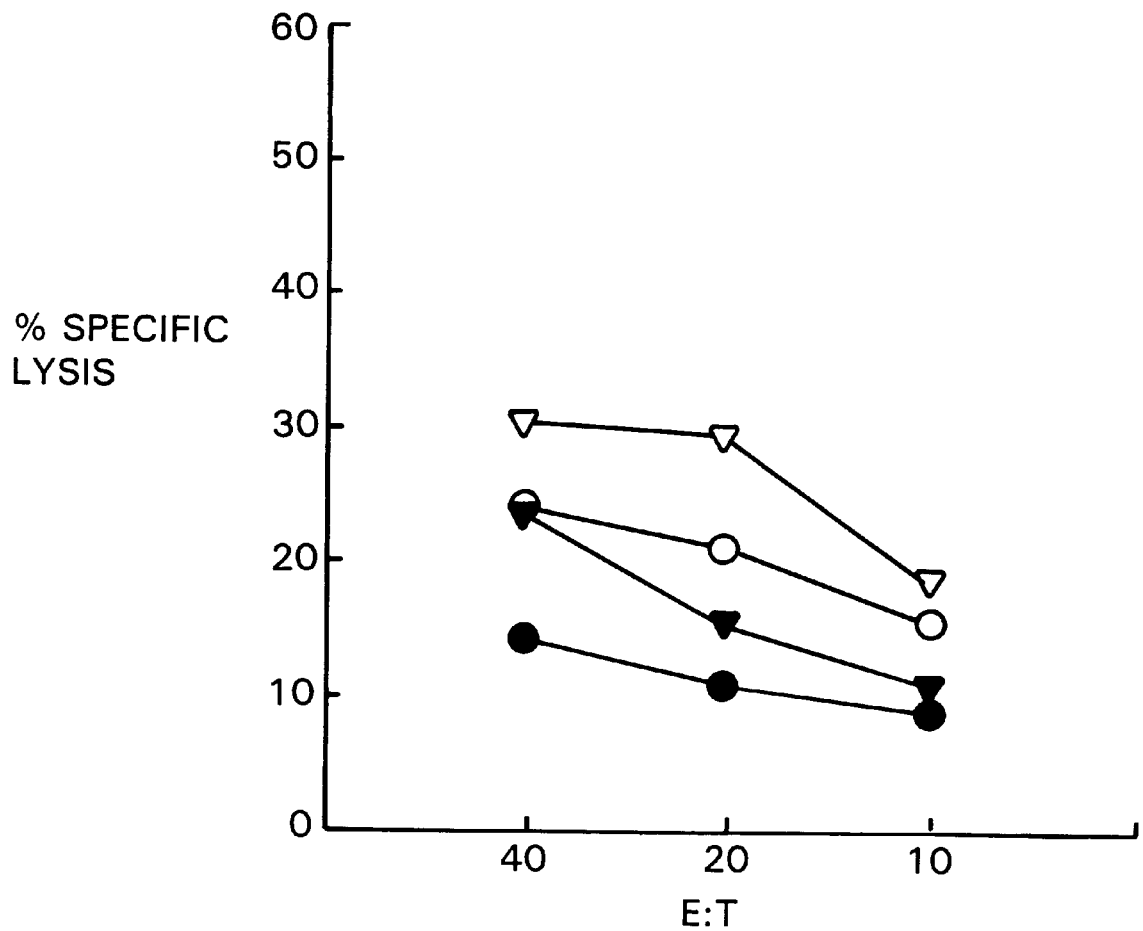

In Vitro Recognition and Lysis of Peptide-Pulsed Tumor Targets by αPAX-3/FKHR Cytotoxic T Cells Generated by Peptide-Pulsed Spleen Cell Immunization This experiment was performed as described above for the αEWS/FLI cells, except that P815 ($H-2^d$) cells were labeled with sodium chromate and the peptide used for pulsing the cells was PAX-3/FKHR. Results are shown in FIG. 13.

EXAMPLE III

Adoptive Transfer Studies

Two studies have been conducted to ascertain the efficacy of tumor suppression by peptide-pulsed spleen cells. In the first study, BALB/c mice were immunized with PAX-3/FKHR peptide-pulsed spleen cells or mock immunized with HBSS. Four weeks later, these animals were challenged with either CT26.W or CT26P/F8. Fifteen days after tumor challenge, the animals were euthanized, the lungs were stained and metastatic tumor nodules were counted. Results of this study are presented in Table 4.

In the second study, the adoptive transfer was accomplished after transplantation of the tumor cells. BALB/c mice were challenged with either CT26.W or CT26P/F8 (Day 0). Three days later (D3), mice received $2 \times 10^7$ spleen cells (i.v.) obtained from animals immunized with PAX-3/FKHR peptide-pulsed spleen cells or mock immunized with HBSS (4 wk post-immunization). Nine days later (D12), the animals were euthanized, the lungs were stained and metastatic tumor nodules were counted. Results of this study are presented in Table 5.

TABLE 4

Summary of PAX-3/FKHR in vivo tumor challenge study

| Treatment Group | Number of Lung Tumor Metastatic Nodules | | | |
|---|---|---|---|---|
| Immunization | A | B | C | D |
| Tumor Challenge | Mock CT26.W | Mock CT26P/F8 | PAX-3/FKHR CT26.W | PAX-3/FKHR CT26P/F8 |
|  | 300[a] | 100 + μ[b] | 300 | 61 |
|  | 213 | 250 | 300 | 51 |
|  | 300 | 111 + μ | 181 | 70 |
|  | 134 | 104 + μ | 300 | 17 |
|  | 239 | 132 + μ | 300 | 17 |
| mean | 237.2 | 141.4 | 276.2 | 43.2[c] |

[a]- The maximum number of metastatic lung nodules able to be discerned was 300.
[b]- The presence of micrometastatic disease was obvious, but only semiquantitative.
[c]- The mean of treatment group D differs from the means of groups A, B, and C at the P = 0.05 level. The means of groups A, B, and C do not differ significantly from each other.

TABLE 5

Summary of adoptive transfer study involving PAX-3/FKHR

| | Number of Lung Tumor Metastatic Nodules | | | |
|---|---|---|---|---|
| Treatment Group | A | B | C | D |
| Tumor Challenge | CT26.W | CT26P/F8 | CT26.W | CT26P/F8 |
| Adoptive Transfer[a] | naive | naive | immunized | immunized |
|  | 100 IC[b] | 16 + μ[c] | 300[d] | 0 |
|  | 300[c] | 36 | 300 | 0 |
|  | 300 | 200 + μ | 200 IC | 83 |
|  | 300 | 200 + μ | 300 | 142 |
|  |  |  | 300 | 87 |
| mean | 250 | 113 | 277.4 | 62.4[e] |

[a]- Mice received $2 \times 10^7$ spleen cells i.v. from either unimmunized animals or animals that had been immunized with PAX-3/FKHR peptide-pulsed spleen cells (10 mM pulse; $1 \times 10^7$ spleen cells i.v.) 4 weeks prior to transfer.
[b]- Incomplete staining of lung, only stained sections were quantitated.
[c]- The presence of micrometastatic disease was obvious, but only semiquantitative.
[d]- The maximum number of metastatic lung nodules able to be discerned was 300.
[e]- The mean of treatment group D differs from the means of groups A and C at the P = 0.05 level.

These in vivo studies demonstrate that mice immunized with PAX-3/FKHR peptide-pulsed spleen cells were partially protected when challenged with CT26P/F8 but were not protected I challenged with CT26.W. Furthermore, unimmunized animals were not protected when challenged with CT26.W or CT26P/F8. These results show that immunization offers tumor-specific therapeutic benefit. In addition, animals bearing established disease, CT26.W or CT26P/F, were treated with adoptively transferred cells obtained from either unimmunized mice or from mice immunized with PAX-3/FKHR peptide-pulsed spleen cells. Those animals which had established disease from CT26P/F8 and received cells adoptively transferred from immunized animals had no disease or greatly reduced tumor burden. Similar studies using EWSIFLI 1 type 4 are underway. These data demonstrate the potential for the treatment of established disease and for recurrent disease, which is a particular problem with these tumors. This approach also provides a specific treatment for these devastating childhood tumors with much less toxic than chemotherapy.

EXAMPLE IV

Induction of $CD8^+$ CTL by Immunization With Syngeneic Irradiated HIV-1 Envelope Derived Peptide-Pulsed Dendritic Cells For many viruses, the greatest anti-viral immunity arises from natural infection, and this immunity has been best mimicked by live attenuated virus vaccines. However, in the case of HIV, such live attenuated organisms may be considered too risky for uninfected human recipients because such retroviruses have the potential risks of integrating viral genome into the host cellular chromosomes, and of inducing immune disorders. To reduce these risks, an alternative is to use pure, well-characterized proteins or synthetic peptides that contain immunodominant determinants for both humoral and cellular immunity. An important component of cellular immunity consists of class I MHC restricted $CD8^+$ cytotoxic T lymphocytes (CTL) that kill virus infected cells and are thought to be major effectors for preventing viral infection.

However, to prime such class I-MHC molecule restricted $CD8^+$ CTL with non-living antigen, such as a recombinant molecule or synthetic peptide, has been thought very difficult to accomplish. We have reported that we could prime $CD8^+$CTL by immunizing with immuno-stimulating complexes (ISCOMS) containing purified intact recombinant gp160 envelope glycoprotein of HIV-1 (45). Several recent pieces of evidence (46–48) indicate that certain antibodies against HIV-1 envelope gp160 protein may enhance infectivity of the virus for monocytes and macrophages. These observations suggest that intact gp160 may have a risk of inducing deleterious antibodies. Therefore, an artificial vaccine construct might be preferable containing only antigenic determinants that could induce CD8$^+$ CTL as well as neutralizing antibodies and helper T cells.

We have identified an immunodominant determinant for CTL in the gp160 envelope protein in mice (21) that is also seen by human CTL (49). In addition, the same epitope is recognized by the major neutralizing anti-bodies (50–52) and by helper T cells (53). Thus, the synthetic peptide containing this determinant can be a good candidate for a subunit vaccine or a component thereof. Making use of the fact that CTL precursors do not seem to distinguish between virus-infected cells and virus-derived peptide-pulsed cells, we show here the requirements for eliciting CD8$^+$ CTL specific for this viral epitope by a single low-dose immunization with peptide-pretreated irradiated syngeneic cells, in particular dendritic cells (DC), without using any harmful adjuvant.

Mice. BALB/c (H-2$^d$), mice were obtained from Charles river Japan Inc. (Tokyo Japan). Mice were used at 6 to 12 wk of age for immunization.

Recombinant Vaccinia Viruses. vSC-8 (recombinant vaccinia vector containing the bacterial lacZ gene), and vSC-25 (recombinant vaccinia vector expressing the HIV env glycoprotein gp160 of the HTLV IIIB isolate without other HIV structural or regulatory proteins) have been described previously (54).

Transfectants. BALB/c.3T3 (H-2$^d$) fibroblast transfectants expressing HIV-1 gp160 of IIIB isolate and control transfectants with only the selectable marker gene were derived as described previously (21) Also, mouse L-cell (H-2$^k$) cell clones stably transfected with H-2D$^d$ (T4.8.3) (18), H-2L$^d$ (T.1.1.1) (18), and H-2K$^d$ (B4III2) (20) were used to determine class I MHC restriction of generated CTL.

Dendritic cells (DC). As described by Steinman et al (55), DC were isolated from nonadherent spleen cells after overnight culture of fresh adherent spleen cells in tissue culture plates. Briefly, spleen cells were fractionated an a discontinuous gradient of BSA (r=1.080). The low-density fraction was allowed to adhere on a plastic dish for 2 hr, and non-adherent cells were discarded and medium was replaced. After an additional 18 hr incubation, non-adherent cells were collected and contaminating macrophages and B cells were removed by resetting with antibody-coated sheep red blood cells.

B cell Preparation. B cells were prepared from spleen cells of unprimed mice by removal of other antigen presenting cells by passage over Sephadex G-10 columns, and by depletion of T cells by treatment with anti-Thy-1 antibody plus complement, as described previously (56).

Monoclonal Antibodies (mAb). The following mAb were used: anti-CD4 (RL172.4; rat IgM) (57), anti-CD8 (3.115; rat IgM) (16, anti-A$^d$ & E$^d$ (M5/114; rat IgM) (58).

Peptide Synthesis and Purification. Peptide 18IIIB was synthesized by solid phase techniques by Peninsula Laboratories, Balmont, Calif., and has a single peak by reverse phase HPLC in 2 different solvent systems, as well as thin layer chromatography, and had the appropriate amino acid analysis. Other peptides were synthesized on an Applied Biosystems 430A synthesizer using standard t-BOC chemistry (59), and purified by gel filtration and reverse phase HPLC.

CTL Generation. Immunizations were carried out either subcutaneously (s.c.) in the base of the tail, or intraperitoneally (i.p.), or intravenously (i.v.) from the tail vein with 27 G needle. Several weeks later, immune spleen cells ($5\times10^6$/ml in 24-well culture plates in complete T-cell medium (a 1:1 mixture of RPMI 1640 and EHAA medium containing 10% FCS, 2 mM L-glutamine, 100 U/ml penicillin, 100 $\mu$g/ml streptomycin and $5\times10^{-5}$M 2-mercaptoethanol)) were restimulated for 6 days in vitro with mitomycin-C treated HIV-1-IIIB envelope gp160 gene transfected histocompatible BALB/c.3T3 fibroblasts alone or in the presence of 10% Rat Con-A supernatant-containing medium (Rat T-cell Monoclone) (Collaborative Research, Inc., Bedford, Mass.) or 10 U/ml of recombinant mouse IL-2 (rIL-2) (Genzyme, Boston, Mass.).

CTL assay. After culture for 6 days, cytolytic activity of the restimulated cells was measured as previously described (21) using a 6 hr assay with various $^{51}$Cr-labelled targets, as indicated in the figure legends. For testing the peptide specificity of CTL, effectors and $^{51}$Cr-labelled targets were mixed with various concentrations of peptide at the beginning of the assay or pulsed with 1 $\mu$M of the target peptide for 2 hours. The percent specific $^{51}$Cr release was calculated as 100 (experimental release—spontaneous release)/(maximum release—spontaneous release). Maximum release was determined from supernatants of cells that were lysed by addition of 5% Triton-X 100. Spontaneous release was determined from target cells incubated without added effector cells. Standard errors of the means of triplicate cultures was always less than 5% of the mean.

Figure 4A:
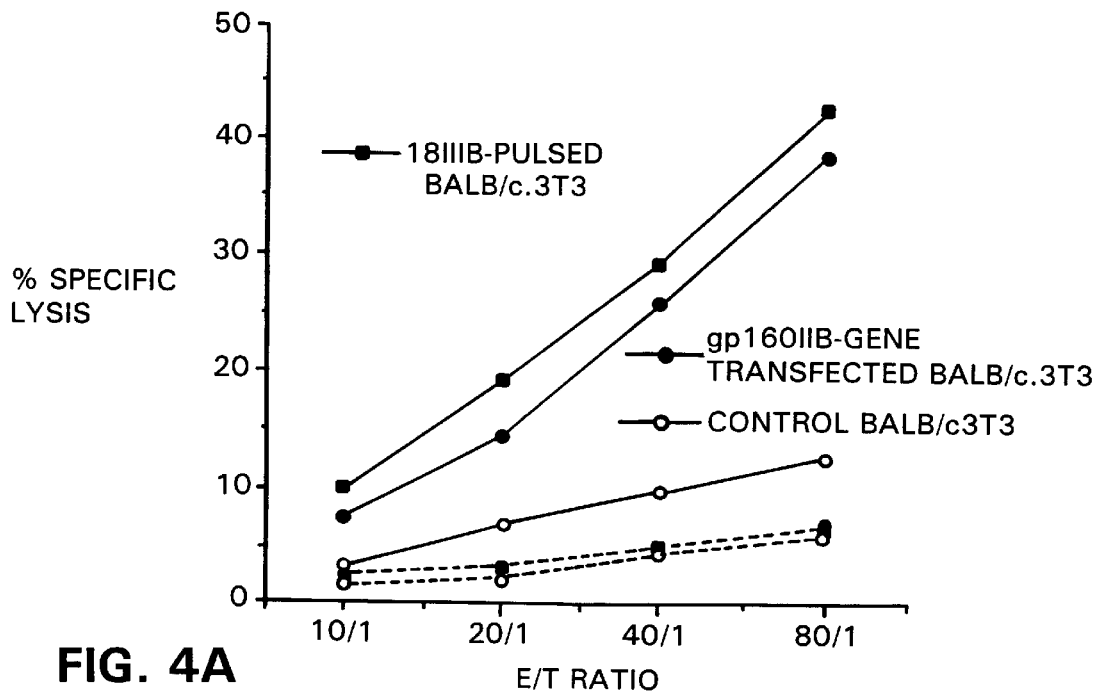
FIG. 4A is a line graph showing induction of epitope-specific CTL by immunization with peptide-pulsed syngeneic spleen cells. Five×10$^7$/ml of BALB/c spleen cells were incubated with 5 μM peptide 18IIIB in 1 ml of 10% fetal calf serum containing RPMI1640 for 2 hours. Then the peptide-pulsed spleen cells were either 3300-rad irradiated (solid lines) or unirradiated (dotted lines) and washed twice with RPMI1640. The cell number was adjusted to 2–4×10$^7$/ml in PBS and 0.2 ml of the treated cells (4–8×10$^6$) were innoculated intravenously into syngeneic BALB/c mice. After 3–4 weeks, immune spleen cells were restimulated in vitro with mitomycin-C treated HIV-1-IIIB envelope gp160 gene transfected syngeneic BALB/c.3T3 fibroblasts with or without interleukin 2 (IL-2). After 6-d culture, cytotoxic activities were tested against the indicated $^{51}$Cr-labeled targets: 1 μM 18IIIB-pulsed BALB/c.3T3 fibroblasts (■); HIV-1-IIIB gp160-gene transfected BALB/c.3T3 (●); and control BALB/c.3T3 fibroblasts (○).

Induction of Epitope-Specific CTL by Immunization Intravenously With Syngeneic Irradiated HIV-1 Envelope Derived Peptide-Pulsed Spleen Cells As a model peptide to elicit specific CTL, we selected peptide 18IIIB (RIQRGPGRAFVTIGK), which we have previously identified as an immunodominant CTL epitope from the human immunodeficiency virus type 1 of IIIB isolate (HIV-1-IIIB) envelope glycoprotein gp160 seen by murine and human CTL (21,49). This peptide is recognized by class I MHC molecule (D$^d$)-restricted murine CD8$^+$ CTL (60) or by HLA-A2 or A3 molecule-restricted human CD8$^+$ CTL (49). Five$\times10^7$/ml of BALB/c spleen cells which express D$^d$ molecules were incubated with 5 $\mu$M peptide 18IIIB in 1 ml of 10% fetal calf serum containing RPMI1640 for 2 hours, sufficient time for association of this peptide with MHC molecules. Then the peptide-pulsed spleen cells were 3300-rad irradiated and washed twice with RPMI1640 to remove free peptide. The cell number was adjusted to $2$–$4\times10^7$/ml and 0.2 ml of the treated cells ($4$–$8\times10^6$) were innoculated intravenously into syngeneic BALB/c mice. After 3–4 weeks, immune spleen cells were restimulated in vitro with mitomycin-C treated HIV-1-IIIB envelope gp160 gene transfected syngeneic BALB/c.3T3 fibroblasts with or without interleukin 2 (IL-2). Highly specific CTL that could kill fibroblast targets either expressing the whole HIV-1 gp160 envelope gene or pulsed with a 15-residue synthetic peptide 18IIIB were generated (FIG. 4A). In a kinetic analysis of this immunization method for CTL induction, highly specific CTL activity was obtained from one month to at least three months after the immunization, and some activity remained at six months (Table 6). Between one to two weeks after the immunization, we sometimes observed non-specific or very weak CTL activity. This may be because it takes some time to prime CD8$^+$ CTL precursors with peptide-pulsed cells in vivo, or because CTL are primed outside the spleen and migrate there only sometime later.

TABLE 6

| Duration after immunization[1] | E/T ratio | Targets (% specific lysis) | | |
|---|---|---|---|---|
| | | gp160IIIB-transfected BALB/c.3T3 | 18IIIB-sensitized BALB/c.3T3 | Normal BALB/c.3T3 |
| 1 week | 80/1 | 24.3 | 27.5 | 28.0 |
| | 40/1 | 15.0 | 19.7 | 20.2 |
| | 20/1 | 10.7 | 14.6 | 13.6 |
| 2 week | 80/1 | 12.2 | 6.2 | 3.7 |
| | 40/1 | 7.5 | 3.7 | 2.3 |
| | 20/1 | 4.7 | 2.0 | 2.5 |
| 4 week | 80/1 | 44.1 | 46.8 | 7.2 |
| | 40/1 | 33.1 | 31.6 | 2.6 |
| | 20/1 | 24.1 | 21.2 | 1.9 |
| 2 month | 80/1 | 49.0 | 64.4 | 9.1 |
| | 40/1 | 31.9 | 46.5 | 5.9 |
| | 20/1 | 28.7 | 31.5 | 3.1 |
| 3 month | 80/1 | 58.9 | 54.2 | 11.7 |
| | 40/1 | 40.5 | 31.8 | 6.3 |
| | 20/1 | 28.0 | 20.4 | 4.0 |
| 6 month | 80/1 | 19.8 | 19.4 | 6.6 |
| | 40/1 | 13.5 | 11.5 | 4.0 |
| | 20/1 | 9.4 | 8.5 | 3.3 |

[1]Immune spleen cells were restimulated with mitomycin-C treated gp160-IIIB gene transfered BALB/c.3T3 fibroblast for 6-day and tested their cytotoxic activities.

Effect of Irradiation of Peptide-Pulsed Spleen Cells on CTL Priming

Figure 4B:
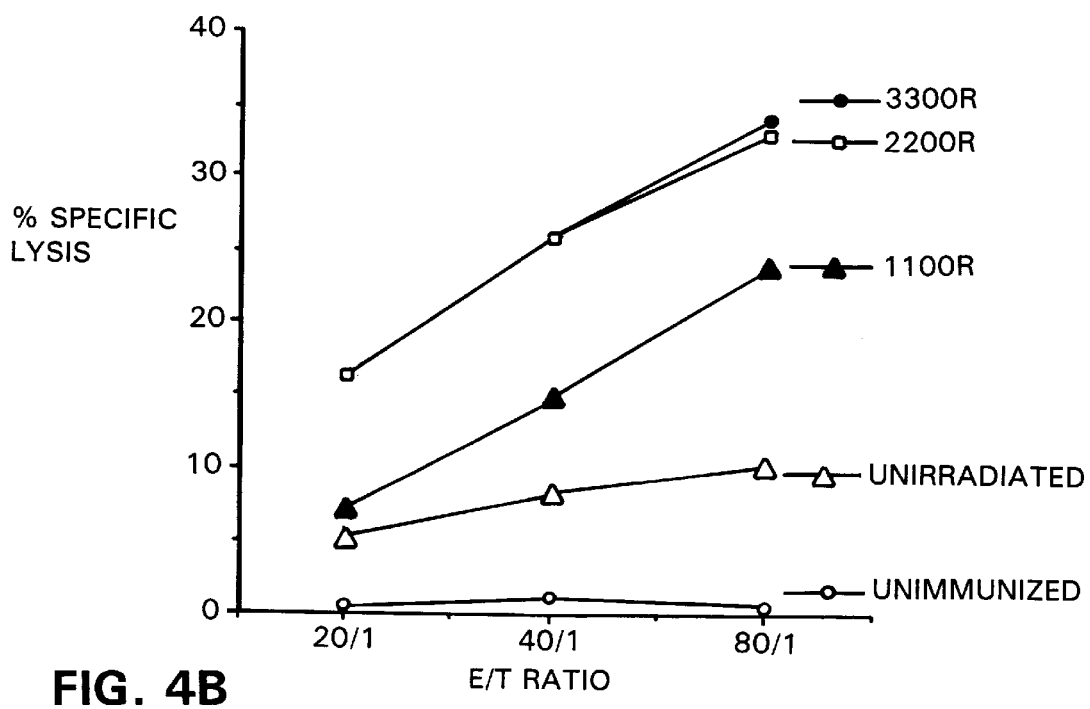
FIG. 4B: The effects of irradiation on CTL priming. Cytotoxic activities were measured against $^{5o}$Cr-labeled HIV-1-IIIB gp160-gene transfected BALB/c.3T3 targets at the indicated effector target ratio. The effector cells were obtained from cultured spleen cells of BALB/c mice immunized with 18IIIB-pulsed spleen cells irradiated 3300 rad (●), 2200 rad (□), 1100 rad (▲), or unirradiated (Δ), or unimmunized control mice (○).

When BALB/c mice were primed intravenously with peptide-pulsed syngenic spleen cells, we found that 3300 rad irradiated cells, not unirradiated cells, induce highly specific CTL (FIG. 4A). To determine the optimal irradiation dose to peptide-pulsed cells for CTL induction, we varied the radiation dose (FIG. 4B). CTL were primed in vivo effectively equally well when the pulsed cells were irradiated with 2200 or 3300 rad, but 1100 rad irradiated cells generated lower CTL activity, albeit still significant compared to un-irradiated cells. This result suggested that i.v.-injected, irradiated (damaged) cells may more easily accumulate in, or home to, the spleen of the immunized mice to present the immuno-genic peptide for priming CD8+ CTL precursors, and these damaged cells may act like virus-infected damaged cells expressing viral antigenic peptide on the surface of the cells. Irradiated cells may be more readily phagocytosed by other cells that actually present the antigen to T cells. Alternatively, because B cells are sensitive to 2200-3300 rad but not 1100 rad (61), it is possible that non-B cells (e.g. macrophages or dendritic cells) are responsible for presentation, and B cells interfere (see below).

Comparison of Route for Immunization with Peptide-Pulsed Spleen Cells

Figure 5:
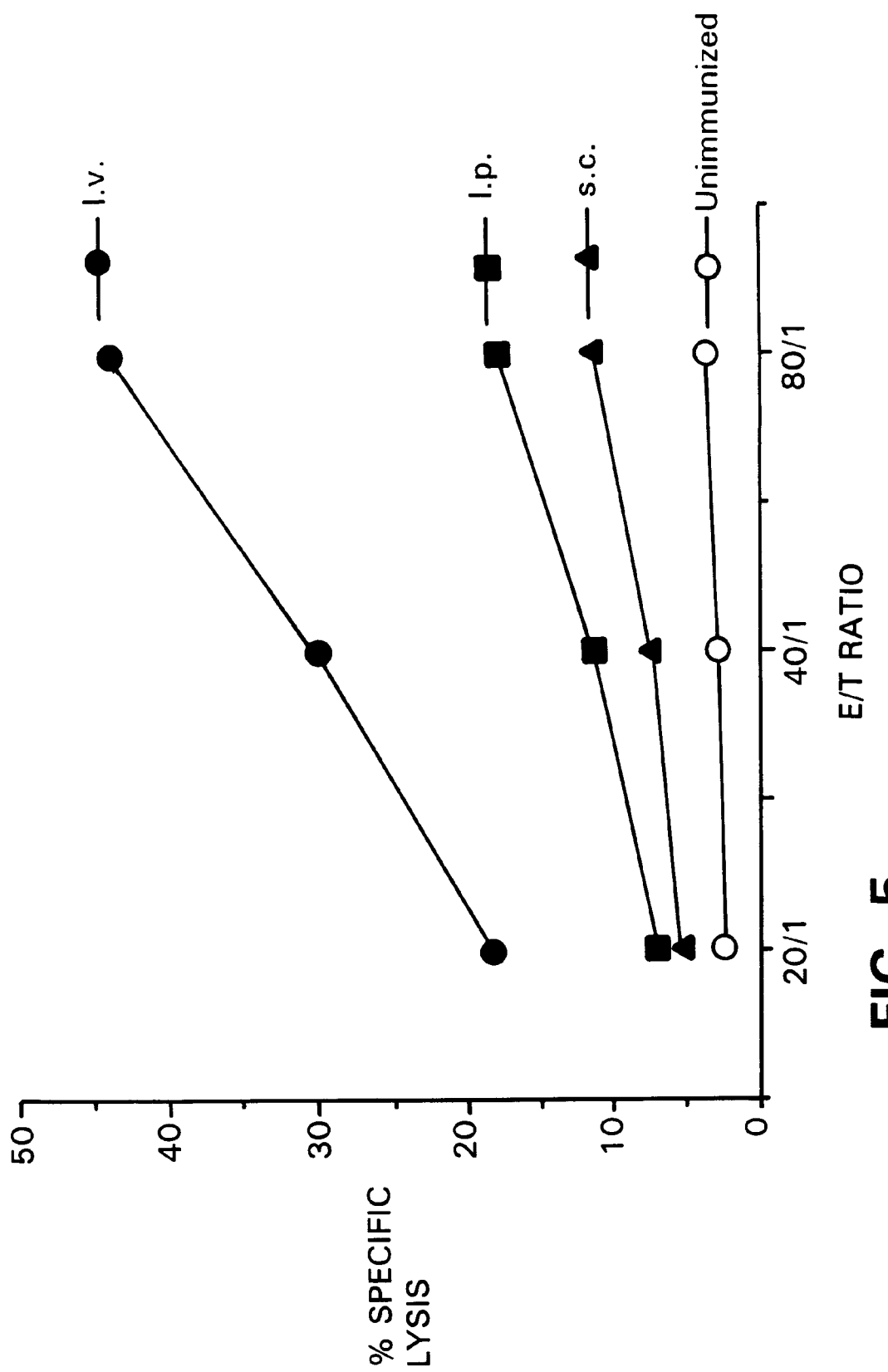
FIG. 5 is a line graph showing a comparison of the route for immunization. Cytotoxic activities were measured against $^{51}$Cr-labeled HIV-1-IIIB gp160-gene transfected BALB/c.3T3 targets at the indicated effector:target ratio. The effector cells were obtained from cultured spleen cells of BALB/c mice immunized with 18IIIB-pulsed 3300 rad irradiated spleen cells intravenously (i.v.) (●), intraperitoneally (i.p.) (■), or subcutaneously (s.c.) (▲), or of unimmunized control mice (○).

To examine the relative efficacy of different routes of immunization for CTL priming, we immunized BALB/c mice intraperitonealy (i.p.), subcutaneously (s.c.), or intravenously (i.v.) with peptide 18IIIB-pulsed syngeneic irradiated spleen cells. Although specific CTL activity was induced to some extent by s.c. or i.p. immunization as compared with unimmunized mice, the level of killing was always much weaker than that induced by intravenous (i.v.) immunization (FIG. 5).

Figure 6:
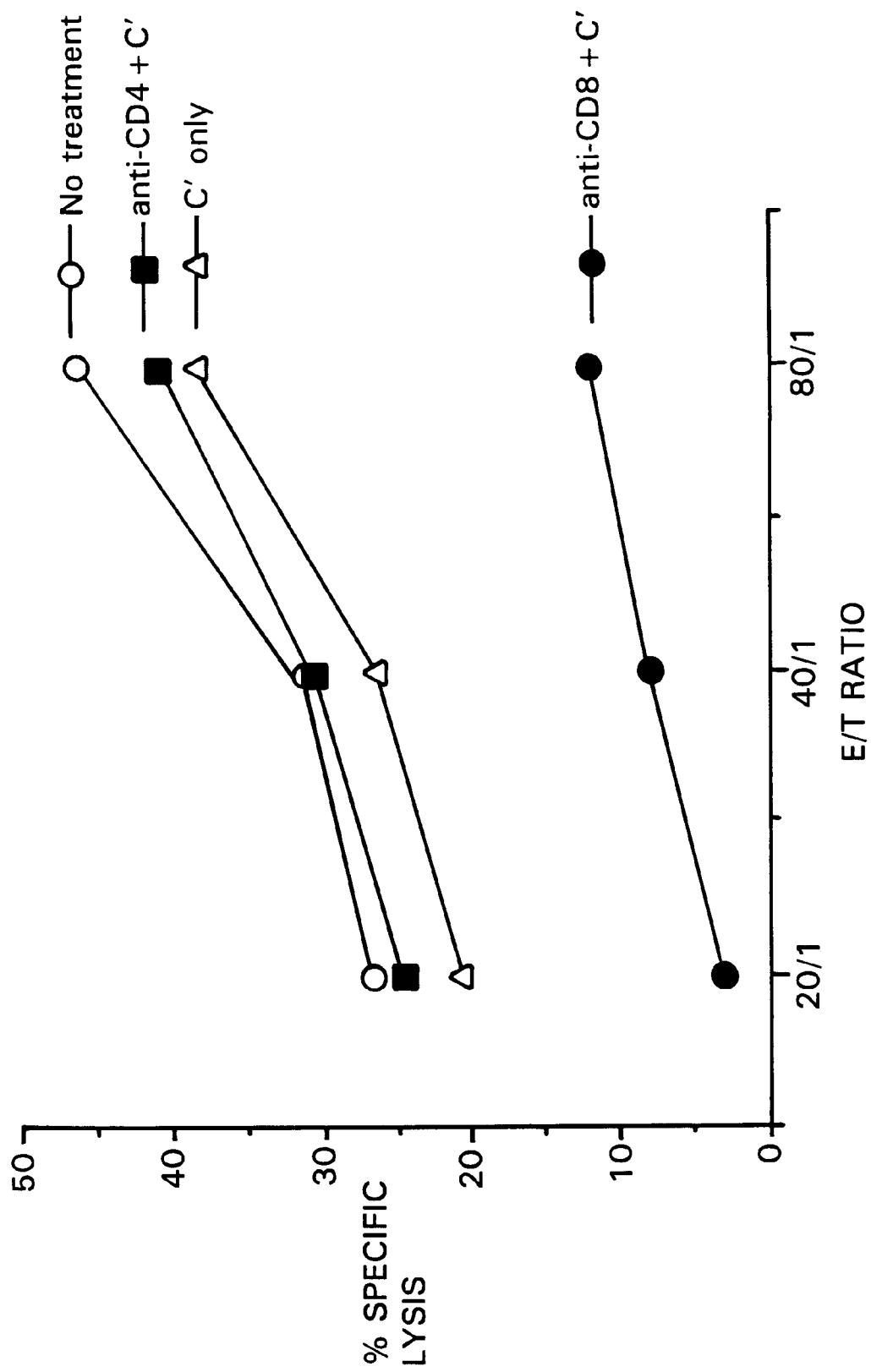
FIG. 6 is a line graph showing the phenotype of the CTL induced by peptide-pulsed-cell immunization. Cytotoxic activities were measured against the same targets as in FIG. 5. The effector cells were pre-treated with anti-CD4 mAb (RL172.4) plus complement (■), anti-CD8 mAb (3.155) plus complement (●), or with complement only (Δ). (○) shows no treatment control.

Phenotype and Class I MHC Restriction of the CTL Induced by Peptide-Pulsed Spleen Cells Immunization Treatment of the CTL effector cells induced by this method with anti-CD8+ monoclonal antibody plus rabbit complement led to complete loss of killing activity on fibroblast targets either expressing the whole gp160 gene of the IIIB strain or pulsed with epitope peptide 18IIIB. However, no effect was observed when the CTL were treated with either anti-CD4+ monoclonal antibody plus complement or complement alone (FIG. 6). In addition, H-$2^k$ L-cell transfectants expressing the $D^d$ class I MHC molecule were killed by the CTL in the presence of peptide 18IIIB, whereas untransfected L cells were not. These data clearly show that CTL effectors induced by this approach are conventional CD4− CD8+ class I MHC-molecule restricted CTL, and recognize peptide 18IIIB with the same class I molecule, $D^d$, as those induced by immunization with live recombinant vaccinia virus expressing the HIV-1 IIIB gp160 envelope gene (21).

Figure 7:
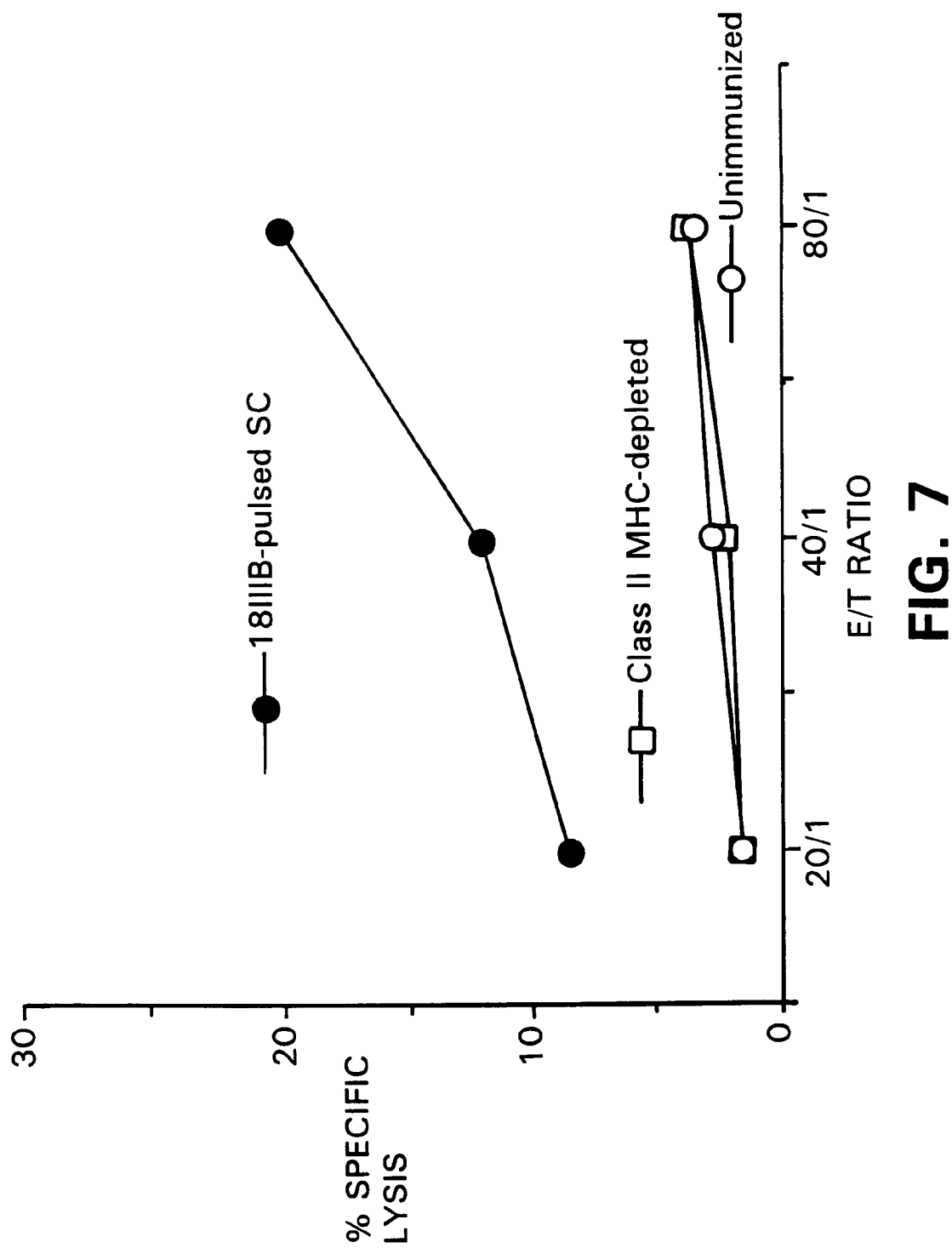
FIG. 7 is a line graph showing a characterization of the cells in the inoculum responsible for in vivo induction of peptide-specific CD8$^+$ CTL. Cytotoxic activities were measured against the same targets as in FIG. 5. The effector cells were obtained from the following mice. BALB/c mice were immunized i.v. with 18IIIB-pulsed irradiated spleen cells pretreated with anti-class II MHC (A$^d$ & E$^d$) mAb (M5/114) plus complement (□) and untreated (●). (○) shows unimmunized control mice.
Figure 8A:
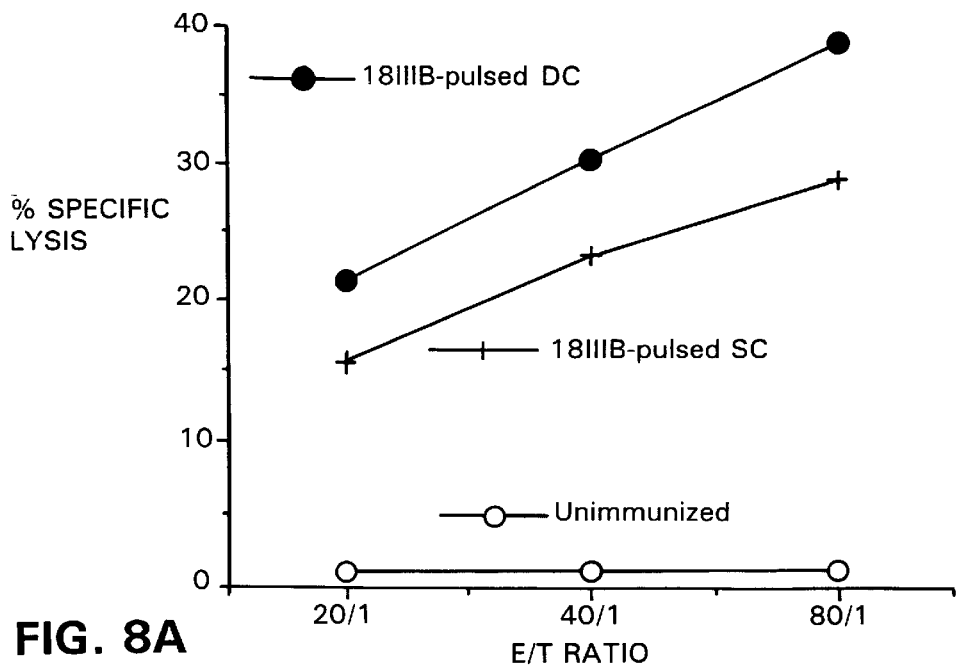
FIG. 8A is a line graph showing induction of highly specific CTL by immunization with 18IIIB-pulsed irradiated DC. Cytotoxic activities were measured against the same targets as in FIG. 5. The effector cells were obtained from cultured spleen cells of BALB/c mice immunized i.v. with 8×10$^6$ 18IIIB-pulsed 3300 rad irradiated spleen cells (+), or 1 ×10$^5$ irradiated DC (●), or from unimmunized control mice (○).
Figure 8B:
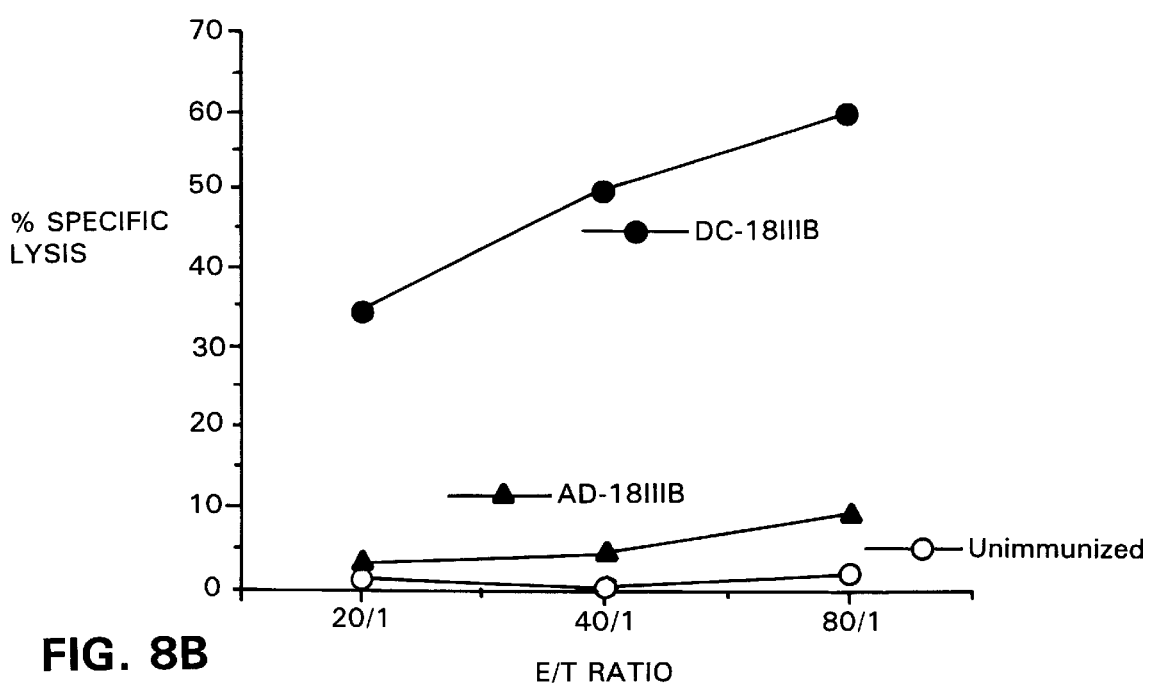
FIG. 8B is a line graph showing a comparison of abilities of adherent macrophages and DC to prime epitope-specific CTL. Peptide 18IIIB-pulsed irradiated splenic adherent cells (1×10$^5$) (▲) after removal of DC were tested for immunization as compared to DC immunization (1×10$^5$) (●). (○) shows unimmunized control mice.
Figure 8C:
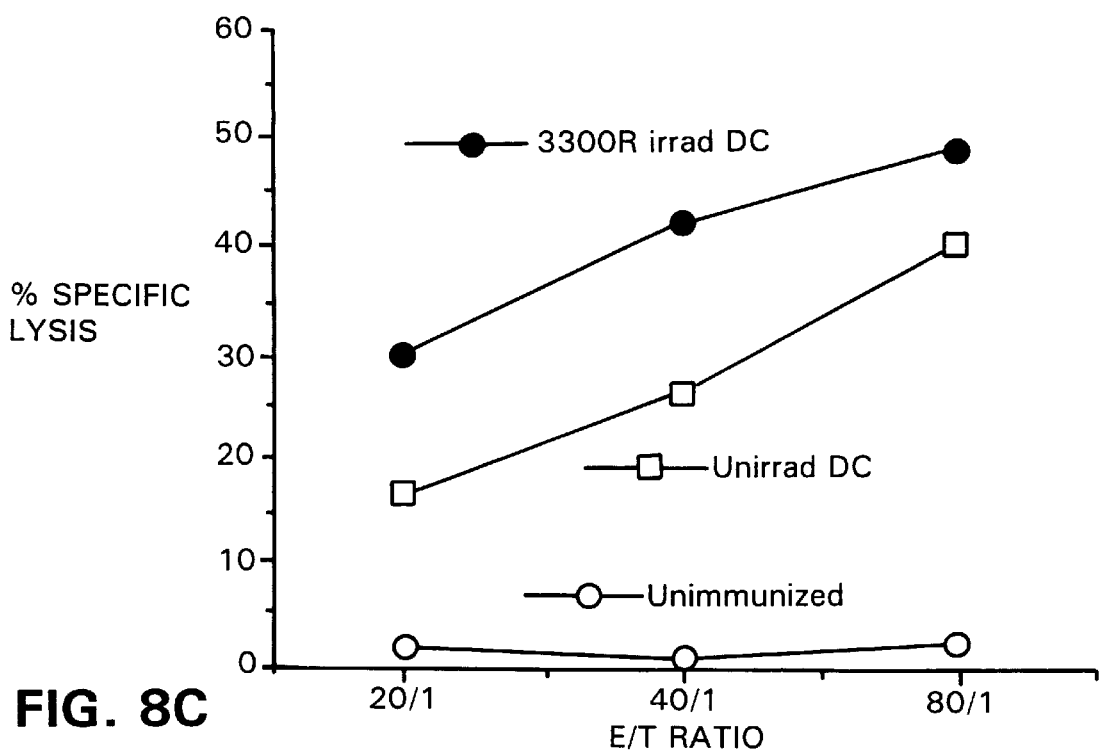
FIG. 8C is a line graph showing the effects of irradiation on DC priming. Immunizations were performed with 3300 rad irradiated DC (●) and unirradiated DC (□). (○) shows unimmunized control mice.
Figure 8D:
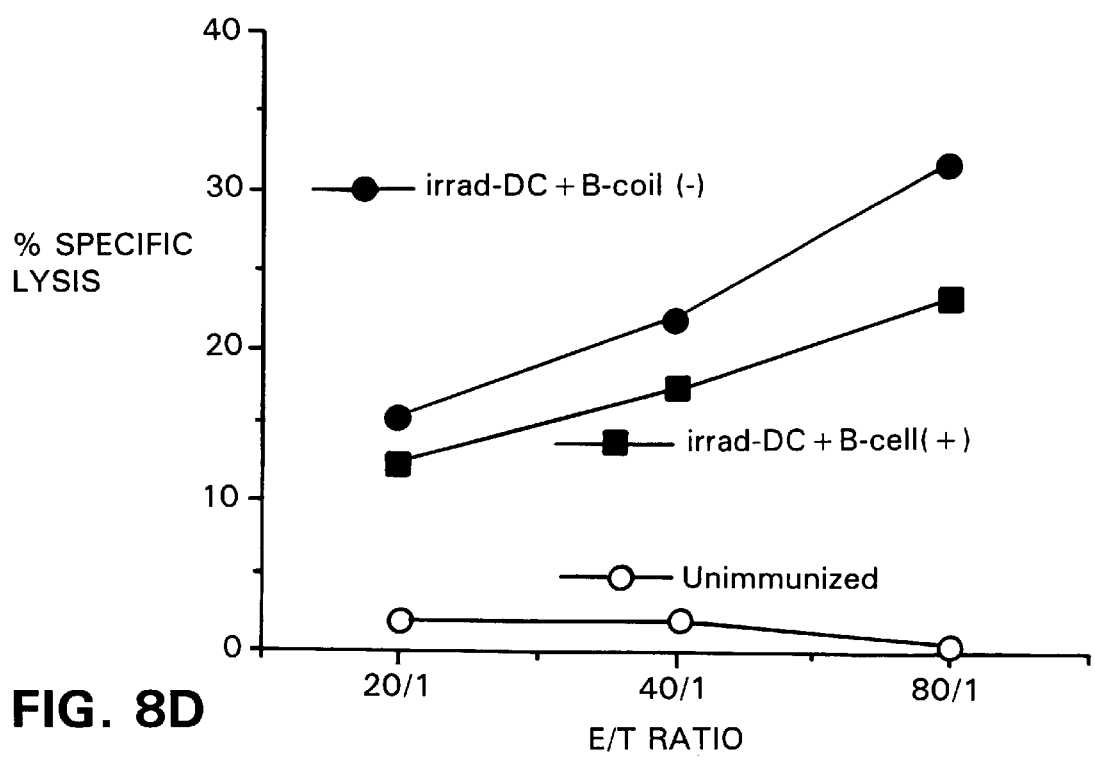
FIG. 8D is a line graph showing the effects of B cells on peptide-pulsed immunization by DC. 2200 rad irradiated DC (2×10$^5$) were co-cultured with (>) or without (●) 1×10$^6$ unirradiated B cells during incubation with peptide 18IIIB before immunization.

Characterization of the Cells in the Inoculum Responsible for in Vivo Induction of Peptide-Specific CD8+ CTL Since most professional antigen-presenting cells (APCs) express class II MHC molecules, we asked whether the cell presenting peptide with class I MHC molecules in this case also was a class II-positive cell. To investigate this question, BALB/c mice were immunized i.v. with 18IIIB pulsed irradiated spleen cells pretreated with anti-class II MHC ($A^d$ & $E^d$) monoclonal antibody (M5/114) plus complement. This treatment almost completely abrogated CTL induction even though re-stimulation was done in the presence of IL-2 (FIG. 7). The results suggest that class II MHC molecule-bearing cells are required to carry viral peptide antigen to prime CD8+CTL and/or that class II MHC molecule-restricted CD4+helper T cells may also need to be primed to elicit class I MHC restricted CD8+CTL. To further characterize the class II positive cells involved, splenic dendritic cells (DC) were pulsed with peptide 18IIIB, 3300 rad irradiated and inoculated intravenously into BALB/c mice via the tail vein. Highly specific CTL activity was observed when the immune spleen cells of these mice were restimulated with mitomycin-C treated BALB/c.3T3 fibroblasts transfected with the HIV-1-gp160 envelope gene (FIG. 8A). In addition, peptide 18IIIB-pulsed irradiated splenic adherent cells after removal of DC were also tested for immunization. In this case, the level of CTL was very low as compared to DC immunization (FIG. 8B). Furthermore, we compared the difference in efficacy between irradiated DC and un-irradiated DC for priming CD8+ CTL. The results consistently showed that better CTL priming could be obtained when irradiated DC were used (FIG. 8C). Thus, among class II MHC molecule bearing cells, dendritic cells are particularly effective in presenting antigenic peptide to prime class I-MHC molecule-restricted CD8+ CTL. Because irradiation enhanced activity, we asked whether radiosensitive B cells might interfere with presentation by DC, as suggested above. We added $1\times10^6$ unirradiated B cells to $2\times10^5$ 2200-rad irradiated DC during incubation with peptide 18IIIB before immunization. Although we observed a slight decrease of CTL activity by this approach, the effect of additional B cells was not sufficient to explain the requirement for irradiation as needed solely to eliminate B cells. (FIG. 8D). In a repeat experiment (not shown), even a 10-fold excess of un-irradiated B cells had no inhibitory effect on the immunization with irradiated DC. Finally, depletion of B cells from spleen cell populations using anti-immunoglobulin and complement failed to obviate the need for irradiation. For all of these reasons, we conclude that the primary function of irradiation is not to eliminate an inhibitory effect of radiosensitive B cells as presenting cells.

The Minimal Size Peptide Recognized by Specific CTL Can Prime CD8+CTL

Several laboratories have reported that the actual epitope peptide recognized by class I MHC molecule-restricted CD8+CTL is composed of around 9 amino acid residues (28,62,63).

Using a series of truncated peptides, we have determined the minimum size of the peptide seen by IIIB-specific CTL as 10 amino acids, 18IIIB-I-10 (residues 318 through 327, RGPGRAFVTI) (64). The epitope peptide 18IIIB recognized by $D^d$ class I MHC molecule-restricted CTL is also seen by $A^d$ class II MHC molecule-restricted helper T cells (53). Although the shorter peptide 18IIIB-I-10 has not been proven to be recognized by helper T cells, results to be reported elsewhere indicate that it can bind to I-$A^d$ and stimulate IL-2 production by CD8-depleted immune spleen cells.

Figure 9:
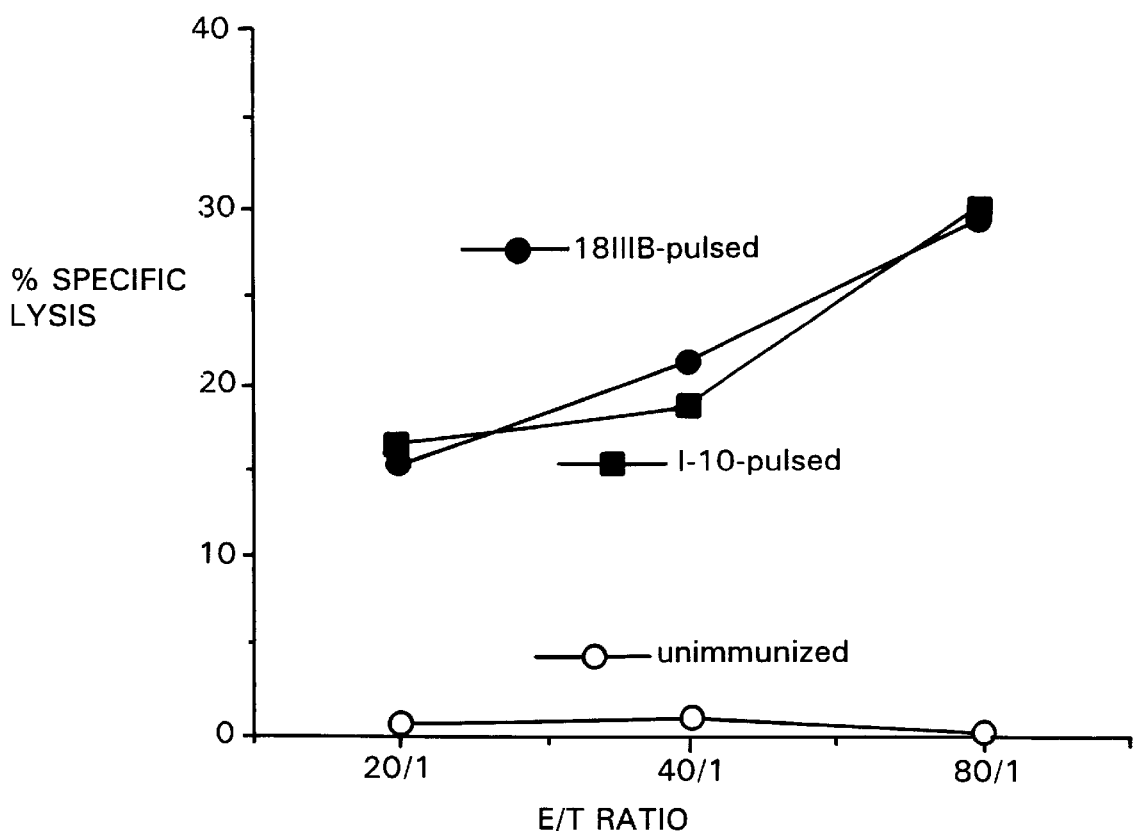
FIG. 9 is a line graph showing that the minimal size peptide recognized by specific CTL can prime CD8$^+$CTL. Cytotoxic activities were measured against the same targets as FIG. 5. DC were pulsed with the minimal 10-mer of peptide 18IIIE-I-10 (RGPGRAFVTI) (>) or 18IIIB (RIQRGPGRAFVTIGK) (●) before immunization for priming CTL. (m) shows unimmunized control mice.

Therefore, we tried to immunize BALB/c mice with irradiated spleen cells pulsed with this shorter peptide. The results clearly demonstrate that the minimal 10-mer of peptide 18IIIB-I-10 can prime $CD8^+$ CTL almost as well as 18IIIB without adding IL-2 exogenously (FIG. 9). Therefore, this shorter peptide 18IIIB-I-10 can be utilized as a peptide vaccine candidate to prime both $CD4^+$ helper T cells and $CD8^+$ CTL.

Figure 10:
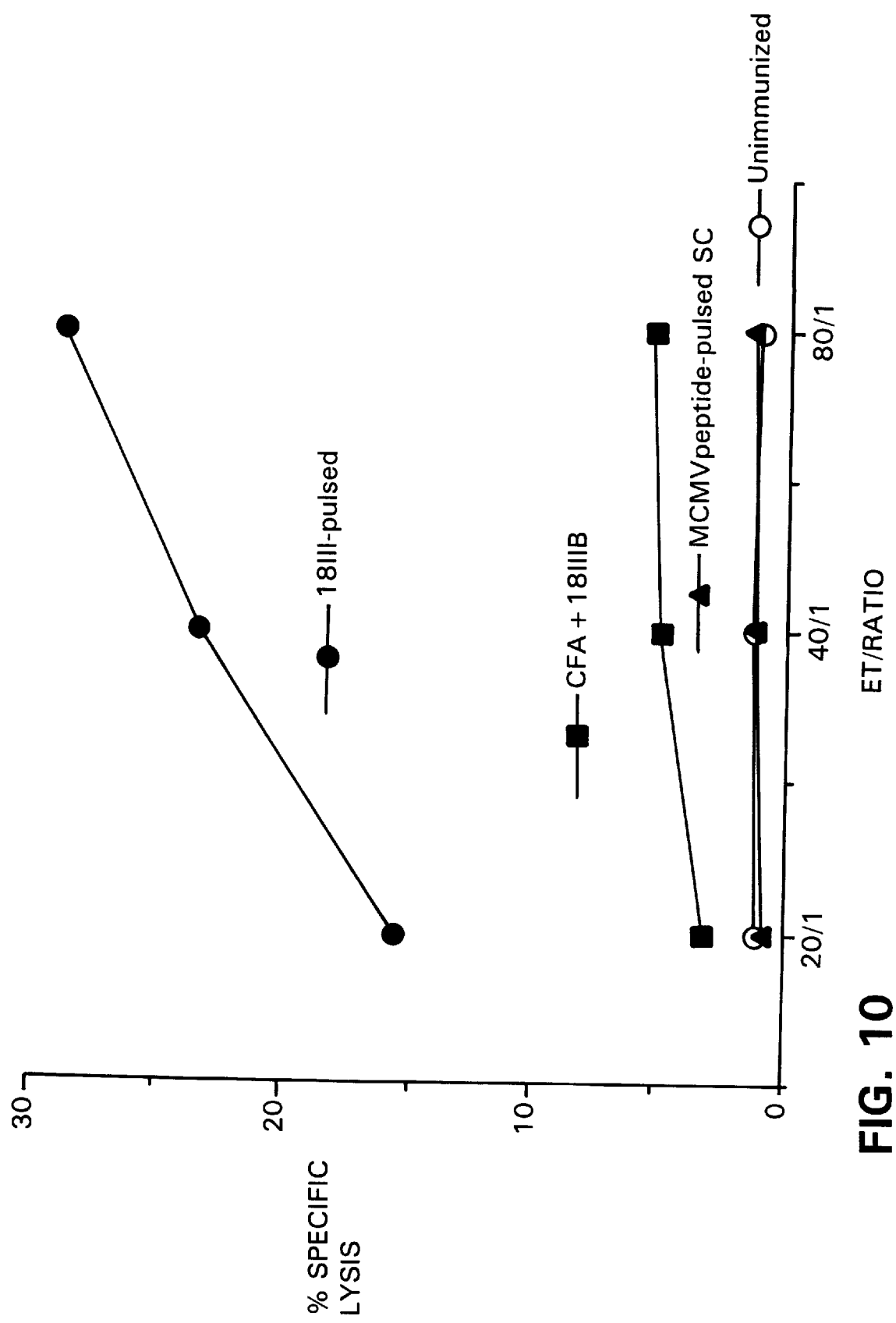
FIG. 10 is a line graph showing a comparison of peptide-pulsed cell immunization with peptide in adjuvant immunization. Cytotoxic activities were measured against the same gp160-gene transfected targets as FIG. 5. BALB/c mice were immunized either with 18IIIB-pulsed syngeneic irradiated spleen cells (●), MCMV (10 μM)-pulsed syngeneic irradiated spleen cells (▲), or with 18IIIB emulsified in CFA (complete Freund's adjuvant) (>). (○) shows unimmunized control mice.

The Difference Between Peptide-Pulsed Cell Immunization and Peptide in Adjuvant Immunization To compare peptide-pulsed cell immunization and conventional peptide-in-adjuvant immunization, we immunized BALB/c mice either with 18IIIB-pulsed syngeneic irradiated spleen cells or with 18IIIB emulsified in CFA (complete Freund's adjuvant). When the immune spleen cells of these mice were restimulated with HIV-1-IIIB gp160 gene transfected BALB/c.3T3 fibroblasts, far stronger CTL activity was obtained in the former group of immune mice (FIG. 10). Therefore, peptide-pulsed cell immunization may prime $CD8^+$ CTL more efficiently than peptide in CFA. As a specificity control, we show mice immunized with spleen cells pulsed with an MCMV peptide, as well as unimmunized mice. Thus, spleen cell immunization does not nonspecifically induce a CTL response, but rather requires the specific peptide.

Figure 11:
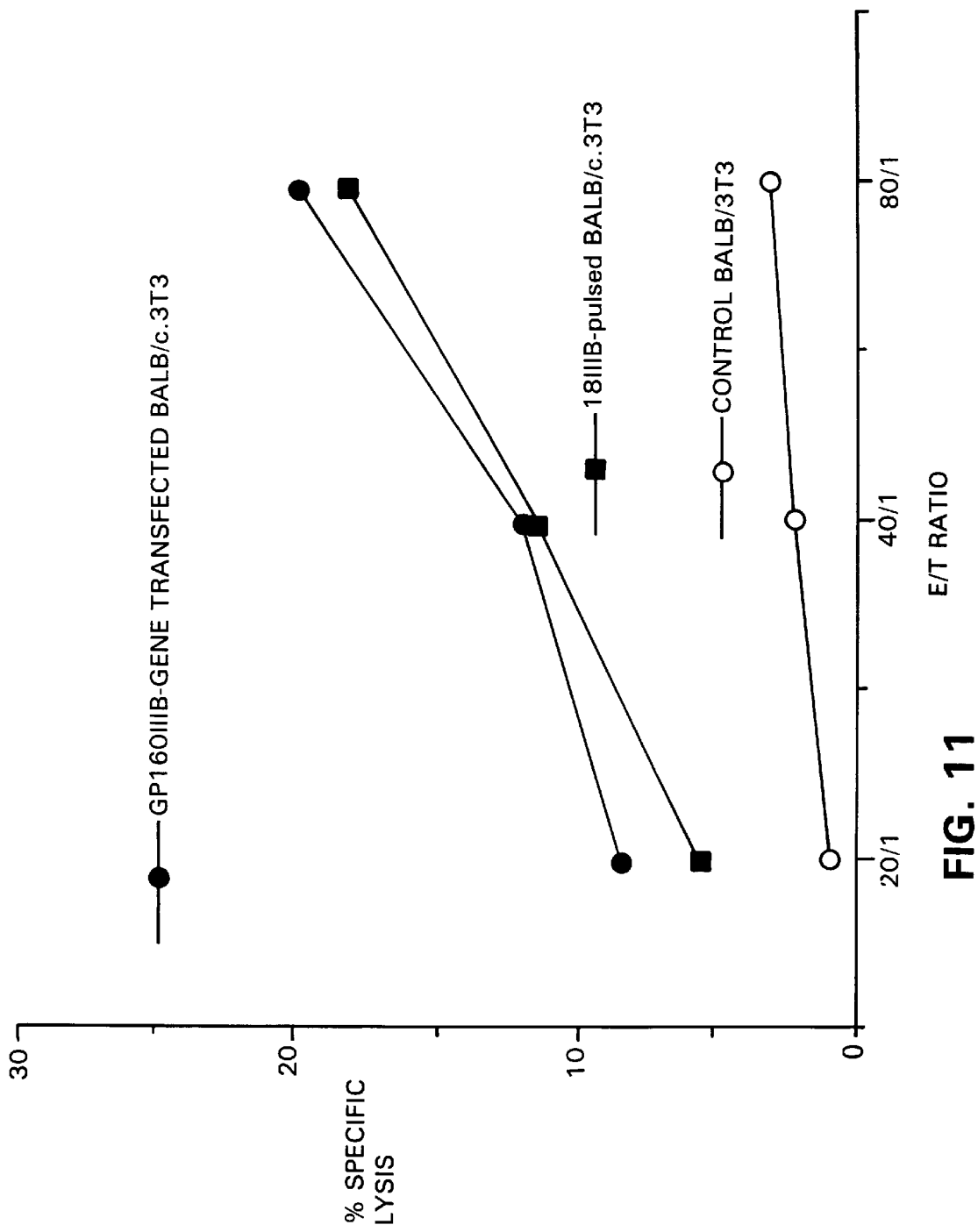
FIG. 11 is a line graph showing that calf serum is not required during the pulsing for effective immunization. Mice were immunized with spleen cells pulsed with P18IIIB in the presence of 1% normal syngeneic mouse serum instead of fetal calf serum, and the resulting effectors restimulated in vitro as in FIG. 4. CTL activity was tested on gp160 IIIB-gene transfected BALB/c 3T3 fibroblast targets (●), or untransfected 3T3 fibroblast targets pulsed with P18IIIB (>), or unpulsed as a control (○).

Immunization with Spleen Cells Pulsed with Peptide in the Presence of Normal Mouse Serum Instead of Fetal Calf Serum Because the spleen cells were always pulsed with peptide in the presence of fetal calf serum, we considered the possibility that the fetal calf serum provided a source of foreign proteins that could be taken up by the dendritic cells and stimulate T-cell help that might contribute to the response. In applying the pulsed cell immunization technique to humans, it would be preferable if it worked in autologous serum, without foreign proteins. To test this possibility, mice were immunized with spleen cells pulsed with P18IIIB in the presence of syngeneic normal mouse serum instead of fetal calf serum, and the resulting effectors tested against fibroblast targets expressing endogenous gp160 or pulsed with P18IIIB peptide (FIG. 11). The result showed that spleen cells pulsed in the presence of normal mouse serum, that had never been exposed to calf serum, were sufficient to elicit peptide-specific CTL. Therefore, exposure to a foreign protein source is not necessary for this activity. We found that we could prime class I $D^d$ molecule-restricted $CD8^+$ CTL when BALB/c mice were injected i.v. with $2\sim4\times10^6$ syngeneic 3300 rad irradiated spleen cells briefly pulsed with an epitope-containing peptide. In comparison with the i.p. or s.c. route, i.v. immunization was most effective at generating CTL activity. It is interesting that we could not induce specific CTL activity without irradiation of the cells before injection. This result may be due to differences in homing patterns of irradiated and unirradiated cells; with irradiation damaged peptide-pulsed cells possibly accumulating in the spleen where CTL precursors may be primed. Alternatively, it may reflect differential radiation sensitivity of different APC populations, B cells being more sensitive to >1100 rad (21). However, since addition of B cells to irradiated DC did not significantly reduce the activity, and B-cell depletion did not substitute for irradiation, this alternative appears less likely.

Staerz and his colleagues (67) have demonstrated that class I MHC restricted $CD8^+$ CTL specific for trypsin digested or CNBr treated ovalbumin can be induced with soluble protein when C57BL/6 mice were immunized intravenously with syngeneic spleen cells incubated with soluble ovalbumin and their immune spleen cells were restimulated in vitro with CNBr-fragmented ovalbumin. They also indicated that they failed to induce such CTL response against EL-4 targets with trypsin digested ovalbumin, whereas immunization with undigested ovalbumin always resulted in response to epitopes exposed by trypsin digestion. These results suggest that trypsinized peptide fragments are antigenic but not immunogenic in this kind of approach.

So far only a few groups have succeeded in eliciting specific $CD8^+$ CTL responses by in vivo immunization with peptides. Deres et al (68) have reported that they could generate influenza virus specific CTL by in vivo priming with synthetic viral peptides covalently linked to a lipid component. Recently, Aichele and co-workers (69) have demonstrated induction of lymphocytic choriomeningitis virus (LCMV) specific class I $L^d$ molecule-restricted $CD8^+$ CTL by three s.c. immunizations with a high dose (100 $\mu$g) of a 15-mer peptide in incomplete Freund's adjuvant (IFA). Using a high dose of a 15-residue peptide derived from Sendai virus nucleoprotein emulsified in IFA for s.c. immunization of B6 mice, Kast et al (41) have also succeeded in priming virus-specific CTL that protected against Sendai virus infection. However, they failed to induce a detectable CTL response by the intravenous injection of free epitopic peptide. Similar results were obtained by Gao and co-workers by s.c. or i.p. immunization with a peptide derived from influenza virus in either complete Freund's adjuvant (CFA) or IFA (70). It is interesting to note that almost every group has indicated a failure to prime CTL by i.v. immunization with free synthetic peptide. However, peptide-pulsed cell immunization appears to be a far more efficient way to prime $CD8^+$ CTL than immunization with CFA plus peptide, and much lower doses of peptide are sufficient after a single immunization.

Our results demonstrate that class II MHC molecule-bearing cells, in particular DC but not adherent macrophages, are the major cells for carrying antigenic peptide to prime $CD8^+$ CTL. Debrick et al. (71) demonstrated that macrophages act as accessory cells for priming $CD8^+$ CTL in vivo using OVA as an antigen, though they found that macrophages do not bind exogenous antigen as peptides. Taken together, we speculate that adherent macrophages may take up exogenous viral antigenic protein or endogenously produce viral protein after infection and present fragmented viral peptide to DC in vivo.

Also, Macatonia et al (72) showed that both primary antiviral proliferative T cell responses and virus-specific CTL can be induced by stimulating unprimed spleen cells with DC infected by influenza virus. Similarly, Melief's group reported that DC are superior to the other cell types in the presentation of Sendai virus to CTL-precursors (73) and that immunization with male H-Y-expressing DC can prime H-Y specific class I-MHC restricted CTL in female mice (74). Likewise, Singer et al. (75) have shown that class II-positive Sephadex G10-adherent cells (macrophages and/ or DC) are important for the CD8+ CTL response to the class I alloantigen K$^{bm1}$. These results indicate that DC may be the key cells to present alloantigens and endogenously synthesized epitopes of viral or minor histocompati-bility gene-derived proteins to class I-restricted CD8+ CTL as well as class II-restricted CD4+ helper T cells. However, these studies did not examine immunization with DC pulsed with defined synthetic peptides. In the case of class II MHC molecules, Inaba et al (76) reported that class II MHC restricted helper T cells can be elicited by footpad immunization with antigen-pulsed DC. Thus, both class II MHC-restricted helper T cells and class I MHC-restricted CTL can be primed in vivo by DC with antigenic peptide. It is noteworthy that priming with pulsed DC by i.v. immunization appears far more potent than by s.c. or i.p. immunization and a single immunization will result in immunity lasting at least 3-6 months. If CTL precursors cannot distinguish between virus-infected cells and viral-peptide pulsed cells on which the appropriate size of trimmed peptide may fit in the groove of class I MHC molecules, this method seems to reflect more closely natural virus infection. From this point of view, this method will be more applicable than other immunization methods in analyzing other natural mechanisms of CTL induction or priming. In addition, from a practical point of view, this may be a useful way for accomplishing synthetic peptide vaccination in that we can elicit virus specific CTL that will be able to kill both virus-derived peptide pulsed targets and targets infected with recombinant vaccinia virus expressing whole gp160 envelope gene without using any harmful adjuvant. Although perhaps not practical for large scale, mass immunizations of whole populations, this method could be applied to specific immuno-therapy of individual patients. Moreover, very recently Harty and Bevan reported (77) that they could protect mice from the Listeria monocygenes infection by the adoptive transfer of CD8+ CTL induced by epitope peptide-pulsed spleen cell immunization as we have shown here, although the specific requirements for effective immunization were not examined. Important for the extension of this method to human immunization, Knight et al (78) have reported that human peripheral mononuclear cells (PBMC) contain many DC, making it possible to use human PBMC, the only cells practical for use in humans. Also, no foreign serum source is necessary during the pulsing (FIG. 11).

The invention being thus described, it will be obvious that the same may be varied in many ways. Such variations are not to be regarded as a departure from the spirit and scope of the invention, and all such modifications as would be obvious to one skilled in the art are intended to be included within the scope of the claims below.

REFERENCES

Each of the publications and patents referred herein below are expressly incorporated herein by reference in their entirety.

Rosenberg, S. (1985) *J. Natl. Cancer Inst.* 75, 595–603.
2. Rosenberg, S. A., Packard, B. S., Aebersold, P. M., Solomon, D., Topalian, S. L., Toy, S. T., Simon, P., Lotze, M. T., Yang, J. C., Seipp, C. A., Simpson, C., Carter, C., Bock, S., Schwartzentruber, D., Wei, J. P. & White, D. E. (1988) N. *Engl. J. Med.* 319, 1676–1680.
3. Lotze, M. T., Custer, M. C., Bolton, E. S., Wiebke, E. A., Kawakami, Y. & Rosenberg, S. A. (1990) *Hum. Immunol.* 28, 198–207.
4. Vogelstein, B. (1990) *Nature* 348, 681–682.
5. de Fromentel, C. C & Soussi, T. (1992) *Genes, Chromosones & Cancer* 4, 1–15.
6. Levine, A. J., Momand, J. & Finlay, C. A. (1991) *Nature* 351, 453–456.
7. Townsend, A. & Bodmer, H. (1989) *Annu. Rev. Immunol.* 7, 601–624.
8. Rötzschke, O. & Falk, K. (1991) *Immunol. Today* 12, 447–455.
9. Monaco, J. J. (1992) *Immunology Today* 13, 173–179.
10. Peace, D. J., Chen, W., Nelson, H. & Cheever(1991) *J. Immunol.* 146, 2059–2065.
11. Jung, S. & Schluesener, H. J. (1991) *J. Exp. Med.* 173, 273–276.
12. Cease, K. B., Berkower, I., York-Jolley, J. & Berzofsky, J. A. (1986) *J. Exp. Med.* 164, 1779–1784.
13. Tam, J. P., Heath, W. F. & Merrifield, R. B. (1983) *J. Am. Chem. Soc.* 105, 6442–6455.
14. Matis, L. A., Longo, D. L., Hedrick, S. M., Hannum, C., Margoliash, E. & Schwartz, R. H. (1983) *J. Immunol.* 130, 1527–1535.
15. Bennink, J. R., Yewdell, J. W., Smith, G. L., Moller, C. & Moss, B. (1984) *Nature* 311, 578–579.
16. Sarmiento, M., Glasebrook, A. L. & Fitch, F. W. (1980) *J. Immunol.* 125, 2665–2672.
17. Wilde, D. B., Marrack, P., Kappler, J., Dialynas, D. P. & Fitch, F. W. (1983) *J. Immunol.* 131, 2178–2183.
18. Margulies, D. H., Evans, G. A., Ozato, K., Camerini-Otero, R. D., Tanaka, K., Appella, E. & Seidman, J. G. (1983) *J. Immunol.* 130, 463.
19. Evans, G. A., Margulies, D. H., Camerini-Otero, R. D., Ozato, K. & Seidman, J. G. (1982) *Proc. Natl. Acad. Sci. U. S. A.* 79, 1994–1998.
20. Abastado, J. -P., Jaulin, C., Schutze, M. -P., Langlade-Demoyen, P., Plata, F., Ozato, K. & Kourilsky, P. (1987) *J. Exp. Med.* 166, 327–340.
21. Takahashi, H., Cohen, J., Hosmalin, A., Cease, K. B., Houghten, R., Cornette, J., DeLisi, C., Moss, B., Germain, R. N. & Berzofsky, J. A. (1988) *Proc. Natl. Acad. Sci. USA* 85, 3105–3109.
22. Chiba, I., Takahashi, T., Nau, M. M., D'Amico, D., Curiel, D. T., Mitsudomi, T., Buchhagen, D. L., Carbone, D., Piantadosi, S., Koga, H., Reissman, P. T., Slamon, D. J., Holmes, E. C. & Minna, J. D. (1990) *Oncogene* 5, 1603–1610.
23. Winter, S. F., Minna, J. D., Johnson, B. E., Takahashi, T., Gazdar, A. F. & Carbone, D. P. (1992) *Cancer. Res.* 52, 4168–4174.
24. Takahashi, T., Nau, M. M., Chiba, I., Birrer, M. J., Rosenberg, R. K., Vinocour, M., Levitt, M., Pass, H., Gazdar, A. F. & Minna, J. D. (1989) *Science* 246, 491–494.
25. Mitsudomi, T., Steinberg, S. M., Nau, M. M., Carbone, D., D'Amico, D., Bodner, S., Oie, H. K., Linnoila, R. I., Mulshine, J. L., Minna, J. D. & Gazdar, A. F. (1992) *Oncogene* 7, 171–180.
26. D'Amico, D., Carbone, D., Mitsudomi, T., Nau, M., Fedorko, J., Russell, E., Johnson, B., Buchhagen, D., Bodner, S., Phelps, R., Gazdar, A. & Minna, J. D. (1992) *Oncogene* 7, 339–346.
27. Romero, P., Corradin, G., Luescher, I. F. & Maryanski, J. L. (1991) *J. Exp. Med.* 174, 603–612.
28. Falk, K., Rötzschke, O., Stevanovic, S., Jung, G. & Rammensee, H. -G. (1991) *Nature* 351, 290–296.
29. DeLisi, C. & Berzofsky, J. A. (1985) *Proc. Natl. Acad. Sci. U. S. A.* 82, 7048–7052.
30. Margalit, H., Spouge, J. L., Cornette, J. L., Cease, K., DeLisi, C. & Berzofsky, J. A. (1987) *J. Immunol.* 138, 2213–2229.
31. Cornette, J. L., Margalit, H., DeLisi, C. & Berzofsky, J. A. (1989) *Methods in Enzymol.* 178, 611–634.

32. Levine, A. J. (1990) *BioEssays* 12, 60–66.
33. Deres, K., Schumacher, T. N. M., Wiesmuller, K. -H., Stevanovic, S., Greiner, G., Jung, G. & Ploegh, H. L. (1992) *Eur. J. Immunol.* 22, 1603–1608.
34. Fremont, D. H., Matsumura, M., Stura, E. A., Peterson, P. A. & Wilson, I. A. (1992) *Science* 257, 919–927.
35. Matsumura, M., Fremont, D. H., Peterson, P. A. & Wilson, I. A. (1992) *Science* 257, 927–934.
36. Guo, H. -C., Jardetzky, T. S., Garrett, T. P. J., Lane, W. S., Strominger, J. L. & Wiley, D. C. (1992) *Nature* 360, 364–366.
37. Silver, M. L., Guo, H. -C., Strominger, J. L. & Wiley, D. C. (1992) *Nature* 360, 367–369.
38. Carbone, F. R., Moore, M. W., Sheil, J. M. & Bevan, M. J. (1988) *J. Exp. Med.* 167, 1767–1779.
39. Townsend, A. R M., Rothbard, J., Gotch, F. M., Bahadur, G., Wraith, D. & McMichael, A. J. (1986) *Cell* 44, 959–968.
40. Germain, R. N. (1986) *Nature* 322, 687–689.
41. Kast, W. K., Roux, L., Curren, J., Blom, H. J. J., Voordouw, A. C., Meloen, R. H., Kolakofsky, D. & Melief, C. J. M. (1991) *Proc. Natl. Acad. Sci. USA* 88, 2283–2287.
42. Schulz, M., Zinkernagel, R. M. & Hengartner, H. (1991) *Proc. Natl. Acad. Sci. U. S. A.* 88, 991–993.
43. Chen, L., Thomas, E. K., Hu, S. -L., Hellström, I. & Hellström, K. E. (1991) *Proc. Natl. Acad. Sci. U. S. A.* 88, 110–114.
44. Alexander, M. A., Damico, C. A., Wieties, K. M., Hansen, T. H. & Connolly, J. M. (1991) *J. Exp. Med.* 173, 849–858.
45. Takahashi, H., Takeshita, T., Morein, B., Putney, S. D., Germain, R. N., and Berzofsky, J. A. (1990). *Nature* 344:873.
46. Robinson, W. E. Jr., Montefiori, D. C., Mitchell, W. M., Prince, A. M., Alter, H. J., Dreesman, G. R., and Eichberg, J. W. (1989). *Proc. Natl. Acad. Sci. U. S. A.* 86:4710.
47. Takeda, A., Tuazon, C. U., and Ennis, F. A. (1988). *Science* 242:580.
48. Robinson, W. E., Jr., Kawamura, T., Gorny, M. K., Lake, D., Xu, J. -Y., Matsumoto, Y., Sugano, T., Masuho, Y., Mitchell, W. M., Hersh, E., and Zolla-Pazner, S. (1990). *Proc. Natl. Acad. Sci. U. S. A.* 87:3185.
49. Clerici, M., Lucey, D. R., Zajac, R. A., Boswell, R. N., Gebel, H. M., Takahashi, H., Berzofsky, J., and Shearer, G. M. (1991). *J. Immunol.* 146:2214.
50. Palker, T. J., Clark, M. E., Langlois, A. J., Matthews, T. J., Weinhold, K. J., Randall, R. R., Bolognesi, D. P., and Haynes, B. F. (1988). *Proc. Natl. Acad. Sci. U. S. A.* 85:1932.
51. Rusche, J. R., Javaherian, K., McDanal, C., Petro, J., Lynn, D. L., Grimaila, R., Langlois, A., Gallo, R. C., Arthur, L. O., Fischinger, P. J., Bolognesi, D. P., Putney, S. D., and Matthews, T. J. (1988). *Proc. Natl. Acad. Sci. U. S. A.* 85:3198.
52. Goudsmit, J., Debouck, C., Meloen, R. H., Smit, L., Bakker, M., Asher, D. M., Wolff, A. V., Gibbs, C. J., Jr., and Gajdusek, D. C. (1988). *Proc. Natl. Acad. Sci. U. S. A.* 85:4478.
53. Takahashi, H., Germain, R. N., Moss, B., and Berzofsky, J. A. (1990). *J. Exp. Med.* 171:571.
54. Chakrabarti, S., Robert-Guroff, M., Wong-Staal, F., Gallo, R. C., and Moss, B. (1986). *Nature* 320:535.
55. Steinman, R. M., Kaplan, G., Witmer, M. D., and Cohn, Z. A. (1979). *J. Exp. Med.* 149:1.
56. Chesnut, R. W. and Grey, H. M. (1981). *J. Immunol.* 126:1075.
57. Ceredig, R., Lowenthal, J. W., Nabholz, M., and MacDonald, H. R. (1985). *Nature* 314:98.
58. Bhattacharya, A., Dorf, M. E., and Springer, T. A. (1981). *J. Immunol.* 127:2488.
59. Stewart, J. M. and Young, J. D. (1984). Solid Phase Peptide Synthesis. 2nd edn. Pierce Chemical Company, Rockford, Ill.
60. Takahashi, H., Houghten, R., Putney, S. D., Margulies, D. H., Moss, B., Germain, R. N., and Berzofsky, J. A. (1989). *J. Exp. Med.* 170:2023.
61. Ashwell, J. D., DeFranco, A. L., Paul, W. E., and Schwartz, R. H. (1984). *J. Exp. Med.* 159:881.
62. Schumacher, T. N. M., De Bruijn, M. L. H., Vernie, L. N., Kast, W. M., Melief, C. J. M., Neefjes, J. J., and Ploegh, H. L. (1991). *Nature* 350:703.
63. Tsomides, T. J., Walker, B. D., and Eisen, H. N. (1991). *Proc. Natl. Acad. Sci. USA* 88:11276.
64. Shirai, M., Pendleton, C. D., and Berzofsky, J. A. (1992). *J. Immunol.* 148:1657.
65. Lie, W. -R., Myers, N. B., Gorka, J., Rubocki, R. J., Connolly, J. M., and Hansen, T. H. (1990). *Nature* 344:439.
66. Reddehase, M. J., Rothbard, J. B., and Koszinowski, U. H. (1989). *Nature* 337:651.
67. Staerz, U. D., Karasuyama, H., and Garner, A. M. (1987). *Nature* 329:449.
68. Deres, K., Schild, H., Wiesmuller, K. H., Jung, G., and Rammensee, H. G. (1989). *Nature* 342:561.
69. Aichele, P., Hengartner, H., Zinkernagel, R. M., and Schulz, M. (1990). *J. Exp. Med.* 171:1815.
70. Gao, X. -M., Zheng, B., Liew, F. Y., Brett, S., and Tite, J. (1991). *J. Immunol.* 147:3268.
71. Debrick, J. E., Campbell, P. A., and Staerz, U. D. (1991). *J. Immunol.* 147:2846.
72. Macatonia, S. E., Taylor, P. M., Knight, S. C., and Askonas, B. A. (1989). *J. Exp. Med.* 169:1255.
73. Kast, W. M., Boog, C. J. P., Roep, B. O., Voordouw, A. C., and Melief, C. J. M. (1988). *J. Immunol.* 140:3186.
74. Boog, C. J. P., Boes, J., and Melief, C. J. M. (1988). *J. Immunol.* 140:3331.
75. Singer, A., Munitz, T. I., Golding, H., Rosenberg, A. S., and Mizuochi, T. (1987). *Immunol. Rev.* 98:143.
76. Inaba, K., Metlay, J. P., Crowley, M. T., and Steinman, R. M. (1990). *J. Exp. Med.* 172:631.
77. Harty, J. T. and Bevan, M. J. (1992). *J. Exp Med.* 175:1531.
78. Knight, S. C., Farrant, J., Bryant, A., Edwards, A. J., Burman, S., Lever, A., Clarke, J., and Webster, A. D. B. (1986). *Immunology* 57:595.
79. Hart, M. K., et al (1991), *Proc. Natl. Acad. Sci., U.S.A.* 88 9448–9452.
80. H-H. Chung et al., (1992) *Science* 259:806–809
81. "Molecular Foundations of Oncology", S. Broder, ed. c. 1991 by Williams and Wilkins, Baltimore, Md.)
82. "Molecular Biology of Lung Cancer", D. P. Carbone and J. D. Minna, chapter 14, ibid.

What is claimed is:

1. A method for immunization, which comprises:
   (i) exposing splenic or peripheral blood mononuclear cells to a peptide, whereby said peptide has a length of at least 9 amino acids and binds to MHC class I molecules on the surface of said mononuclear cells, and wherein said peptide has an amino acid sequence that encompasses the fusion joint of a Ewing's sarcoma (ES)-associated tumor-specific fusion protein encoded by a human chromosomal t(11;22)(q24;q12) translocation or that encompasses the fusion joint of an Alveolar Rhabdomyosarcoma (ARMS) tumor-specific fusion protein encoded by a human chromosomal t(2;3)(q35;q14) translocation;
   (ii) irradiating said mononuclear cells having said peptide bound to MHC class I molecules on their surface; and
   (iii) administering to a mammal the irradiated mononuclear cells having said peptide bound to MHC class I molecules on the their surface.

2. The method of claim 1, wherein said human chromosomal translocation is the t(11;22) (q24;q12) translocation.

3. The method of claim 1, wherein said human chromosomal translocation is the t(2;13)(q35;q14) translocation.

4. The method of claim 1, wherein said peptide has an amino acid sequence comprising a sequence selected from the group consisting of SEQ ID NO: 6, 7, 8, 9, and 10.

5. The method of claim 4, wherein said peptide has an amino acid sequence comprising the sequence of (SEQ ID NO:10).

6. The method of claim 4, wherein said peptide has an amino acid sequence comprising the sequence of SEQ ID NO:9.

7. The method of claim 1, wherein said mononuclear cells are dendritic cells.

8. The method of claim 1, wherein said peptide is a minimal peptide which can bind to said MHC class I molecule.

9. The method of claim 1, wherein said peptide is a peptide which adopts an amphipathic helical conformation in solution.

10. The method of claim 1, wherein said mononuclear cells are irradiated with gamma radiation at a dose of 1500–3500 rad.

11. The method of claim 4, wherein said mononuclear cells are irradiated with gamma radiation at a dose of 1500–3500 rad.

12. The method of claim 1, wherein said cells are administered intravenously.

13. The method of claim 4, wherein said cells are administered intravenously.

14. An immunogen which comprises a population of peripheral blood mononuclear cells coated with a peptide having a length of at least 9 amino acids, which is bound to MHC class I molecules on the surface of said mononuclear cells, wherein said peptide has an amino acid sequence that encompasses the fusion joint of an Ewing's sarcoma (ES)-associated tumor-specific fusion protein encoded by a human chromosomal t(11;22)(q24;q12) translocation or that encompasses the fusion joint of an Alveolar Rhabdomyosarcoma (ARMS)-associated tumor-specific fusion protein encoded by a human chromosomal t(2;3)(q35;q14) translocation, and a pharmaceutically acceptable carrier.

15. An immunogen according to claim 14, wherein said peptide has an amino acid sequence comprising a sequence selected from the group consisting of SEQ ID NO:6, 7, 8, 9, and 10.

16. A peptide having an amino acid sequence selected from the group consisting of SEQ ID NO:6, 7, 8. 9, and 10.

17. A pharmaceutical composition comprising a peptide having an amino acid sequence selected from the group consisting of SEQ ID NO:6, 7, 8, 9, and 10, and a pharmaceutically acceptable carrier.

18. A pharmaceutical composition according to claim 17, wherein said pharmaceutically acceptable carrier comprises an adjuvant or dendritic cells obtained from peripheral blood of a subject.

19. The method of claim 1, wherein the length of the peptide is 9 amino acids.

20. The immunogen of claim 14, wherein the length of the peptide is 9 amino acids.

21. The immunogen of claim 14, wherein the length of the peptide is 9–18 amino acids, inclusive.

22. The immunogen of claim 14, wherein the length of the peptide is 9–18 amino acids, inclusive.

* * * * *